United States Patent
Okada

(10) Patent No.: US 6,326,792 B1
(45) Date of Patent: *Dec. 4, 2001

(54) METHOD AND APPARATUS FOR LIFETIME PREDICTION OF DIELECTRIC BREAKDOWN

(75) Inventor: Kenji Okada, Osaka (JP)

(73) Assignee: Matsushita Electronics Corporation, Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,026

(22) Filed: Sep. 16, 1998

(30) Foreign Application Priority Data

Dec. 25, 1997 (JP) .................................. 9-357095

(51) Int. Cl.[7] .................................. G01N 27/60
(52) U.S. Cl. .................. 324/456; 324/522; 324/537; 324/551; 324/765
(58) Field of Search ................... 324/719, 754, 324/765, 768, 769, 456, 452, 522, 537, 551

(56) References Cited

U.S. PATENT DOCUMENTS

| | | | |
|---|---|---|---|
| 5,594,349 | * 1/1997 | Kimura | 324/551 |
| 5,600,578 | * 2/1997 | Fang et al. | 364/578 |
| 6,043,102 | * 3/2000 | Fang et al. | 438/14 |
| 6,049,213 | * 4/2000 | Abadeer | 324/719 |

OTHER PUBLICATIONS

M. Depas, et al., "Soft Breakdown of Ultra–thin Gate Oxidxe Layers", IEEE Transactions on Electron Devices, vol. 43, No. 9, pp. 1499–1504, Sep. 1996.

K. Okada, "An Experimental Evidence to Link the Origins of "A Mode" and "B Mode" Stress Induced Leakage Current", Extended Abstracts of the 1997 International conference on Solid State Devices and Materials, Hamamatsu, pp. 92–93, 1997.

K. Okada, "Extended Time Dependent Dielectric Breakdown Model Based on Anomalous Gate Area Dependence of Lifetime in Ultra Thin Silicon Dioxides", JPN. J. Appl. Phys. vol. 36, pp. 1443–1447, Mar. 1997.

K. Okada, et al., "Electrical stress–induced variable range hopping conduction in ultra thin silicon dioxides", Applied Physics Letters, vol. 70, No. 3, pp. 351–353, Jan. 20, 1997.

K. Okada, et al., "New Experimental Findings on Stress Induced Leakage Current of Ultra Thin Silicon Dioxides", The 1994 International Conference on Solid State Devices and Materials, Yokohama, pp. 565–567, Aug. 23–26, 1994.

K. Okada, et al., "New Dielectric Breakdown Model of Local Wearout in Ultra Thin Silicon Dioxides", The 1995 International Conference on Solid State Devices and Materials, Osaka, pp. 473–475, Aug. 21–24, 1995.

(List continued on next page.)

*Primary Examiner*—Safet Metjahic
*Assistant Examiner*—Etienne LeRoux
(74) *Attorney, Agent, or Firm*—McDermott, Will & Emery

(57) ABSTRACT

A stressing voltage is applied to a dielectric film (step S23). An A-SILC is monitored with stressing time and is plotted on a log-log scale (step S24). A straight line is applied to the plotting, a stressing time at which the line crosses a predetermined value of the A-SILC (a breakdown threshold) is obtained, and the obtained stressing time is predicted as the lifetime of the dielectric film (step S26).

14 Claims, 17 Drawing Sheets

OTHER PUBLICATIONS

M. Depas, et al., "Soft Breakdown of Ultra–thin Gate Oxidxe Layers", IEEE Transactions on Electron Devices, Vil. 43, No. 9, pp. 1499–1504, Sep. 1996.

K. Okada, "An Experimental Evidence to Link the Origins of "A Mode" and "B Mode" Stress Induced Leakage Current", Extended Abstracts of the 1997 International conference on Solid State Devices and Materials, Hamamatsu, pp. 92–93, 1997.

K. Okada, "Extended Time Dependent Dielectric Breakdown Model Based on Anomalous Gate Area Dependence of Lifetime in Ultra Thin Silicon Dioxides", Jpn. H. Appl. Phys. vol. 36, pp. 1443–1447, Mar. 1997.

K. Okada, et al., "Electrical stress–induced variable range hopping conduction in ultra thin silicon dioxides", Applied Physics Letters, vol. 70, No. 3, pp. 351–353, Jan. 20, 1997.

K. Okada, et al., "New Experimental Findings on Stress Induced Leakage Current of Ultra Thin Silicon Dioxides", The 1994 International Conference on Solid State Devices and Materials, Osaka, pp. 473–475, Aug. 21–24, 1995.

K. Okada, et al., "New Dielectric Breakdown Model of Local Wearout in Ultra Thin Silicon Dioxides", The 1995 International Conference on Solid State Devices and Materials, Osaka, pp. 473–475, Aug. 21–24, 1995.

D.A. Baglee, et al., "The Effects of Write/Erase Cycling on Data Loss in Eeproms", IEEE IEDM 85, pp. 624–626, 1985.

S.H. Lee, et al., "Quasi–breakdown of ultrathin gate oxide under high field stress", IEEE IEDM 94, pp. 605–608, 1994.

K. Okada, "A New Dielectric Breakdown Mechanism in Silicon Dioxides", 1997 Symposium on VLSI technology Digest of Technical Papers, Session 11–1, pp. 143–144, Jun. 9, 1997.

* cited by examiner

METHOD AND APPARATUS FOR LIFETIME PREDICTION OF DIELECTRIC BREAKDOWN

BACKGROUND OF THE INVENTION

The present invention relates to a method and an apparatus for evaluating a dielectric film. In particular, the present invention relates to lifetime prediction of dielectric breakdown.

In accordance with recent improvement in the packing density of semiconductor integrated circuit devices, the feature sizes of device elements have kept on being shrunk. In the field of VLSIs, the thickness of a silicon dioxide ($SiO_2$) film used as a gate oxide has become smaller than 10 nm, and lifetime prediction of such a thin oxide film has become more and more important. As an evaluating method for gate oxides, a constant voltage stressing method or a constant current stressing method is widely used.

With reference to FIG. 18, a conventional constant voltage stressing method will be first described.

First, a stressing voltage $V_0$, a judgement current level $I_0$ and the number N of samples subjected to measurement are set in step S50.

Next, in step S51, a measurement probe is moved to a first sample selected among the plural samples. Then, in step S52, the stressing voltage $V_0$ is applied across a dielectric film of the sample. Subsequently in step S53, the application of the stressing voltage $V_0$ across the dielectric film is retained for a time period of t1 seconds. A leakage current (I) across the dielectric film is measured in step S54. In step S55, whether dielectric breakdown has occurred is determined on the basis of the measured current level I. For example, it is determined that the dielectric breakdown has occurred when the absolute value of the current level I is larger than the judgement current level $I_0$. In the case where it is determined that the dielectric breakdown has not occurred, the measurement procedure returns to step S53, so that the steps S53, S54 and S55 are repeated until the dielectric breakdown is observed. In the case where the breakdown was detected in step S55, a time to breakdown is recorded in step S56.

When the measurement for all the samples is completed in step S57, all of the total stressing times($t_1$ to $t_N$) for the N samples are used to calculate a time $t_{BD}$ in step 58. Weibull plotting can be adopted for such calculation. The Weibull plotting will be described below.

First, values W are calculated on the basis of a cumulative distribution function F and are plotted with regard to each of the stressing times ($t_1$ to $t_N$) on a log scale. In general, the value W represents a cumulative percent of failure, and the cumulative distribution function F represents the probability that the device will fail at or before time t. The value W is given by the following expression (1):

$$W = \ln[\ln\{1/(1-F)\}] \quad (1)$$

It is empirically known that a linear relationship can be obtained between the value W and the stressing time t. More specifically, the measurement data plotted in a Weibull plotting paper shows a linear relationship between broken-down oxides and the time t to the breakdown. Fore example, the stressing time t corresponding to W=50% is easily obtained by Weibull plotting. The obtained stressing time t, or $t_{50}$, means a time when 50% of the oxides has broken down. The Weibull plotting is widely used to estimate the lifetime of dielectric films.

When the measurement of all the N samples is not completed in step S57, the measurement probe is moved to a subsequent sample (step S59), and the measurement procedure returns to step S52. The steps S52 through S59 are then repeated until the measurement of all the N samples is completed.

The sample number N is generally 20 through 100. This is because the measured time t varies among samples, and hence, the time $t_{BD}$ cannot be accurately determined if the sample number N is small.

The time $t_{BD}$ obtained in this manner corresponds to the lifetime of oxide breakdown. Therefore, the time $t_{BD}$ is used for evaluating the quality and reliability of gate oxides.

Next, with reference to FIG. 19, the conventional constant current stressing method will be described.

First, in step S60, a current level $I_0$ for stressing, a critical voltage $V_0$ and the sample numbers N are set and input a measurement apparatus. In step S61, a measurement probe is moved to a first sample.

Next, in step S62, the current $I_0$ is applied to a dielectric film of the first sample. After t1 seconds from the start of the application of the stressing current $I_0$ (step S63), a gate voltage V is measured in step S64. In step S65, it is determined whether or not the oxide breakdown has been caused. For example, when the absolute value of the voltage V is smaller than the absolute value of the critical voltage $V_0$, it is determined that the oxide breakdown has occurred. When it is determined in step S65 that the breakdown has not occurred, the measurement procedure returns to step S62. Then, the steps S63 through S65 are repeated until the oxide breakdown is observed on the first sample.

When the breakdown is detected in step S65, a time t from the start of the current stressing to the oxide breakdown is recorded. When the measurement of all the samples is completed (step S67), the stressing times t with regard to all the samples are used for calculating a lifetime $t_{BD}$ of these samples and a total injected charge $Q_{BD}$ (step S68). The time $t_{BD}$ is determined by using the aforementioned Weibull plotting. Herein, the total injected charge $Q_{BD}$ is defined as a value obtained by dividing a product of the time $t_{BD}$ and the stressing current $I_0$ by an gate electrode area S.

When the measurement of all the samples is not completed in step S67, the measurement probe is moved to a subsequent sample in step S69, so that the procedures in steps S62 through S69 can be repeated until the measurement of all the samples is completed. Also in this case, the sample numbers N is approximately 20 through 100.

In these methods for predicting the lifetime of oxide breakdown, it is disadvantageously necessary to prepare a large number of samples and it takes a disadvantageously long time for the measurement. It is generally known that the measurement error is generally in proportion to $(N^{1/2})/N$. Therefore, when the sample number N is small, the lifetime prediction cannot be reliable. In order to improve the reliability of the lifetime prediction, it is necessary to increase the sample number, which results in an increases in the measurement time.

The object of the present invention is providing a method and an apparatus for evaluating a dielectric film in which the time and the sample number required for measurement can be reduced without degrading the measurement reliability.

SUMMARY OF THE INVENTION

The dielectric film evaluating method of this invention comprises a stressing step of applying electrical stressing to a dielectric film; and a step of monitoring an A mode stress induced leakage current and measuring a value of the A mode stress induced leakage current flowing when breakdown occurs in the dielectric film.

Alternatively, the dielectric film evaluating method of this invention comprises a stressing step of applying electrical stress to a dielectric film in each of plural samples; a step of monitoring an A mode stress induced leakage current and measuring a value of the A mode stress induced leakage current flowing when breakdown occurs in the dielectric film in each of the plural samples; and a threshold determining step of determining a breakdown threshold of the A mode stress induced leakage current by statistically processing the values of the A mode stress induced leakage current measured in the plural samples.

In one aspect, the dielectric film evaluating method of this invention comprises a stressing step of applying electrical stressing to a dielectric film; a step of measuring an A mode stress induced leakage current; and a lifetime predicting step of predicting a lifetime of the dielectric film on the basis of a relationship between the measured value of the A mode stress induced leakage current and a judgement value determined based on a breakdown threshold of the A mode stress induced leakage current.

In another aspect, the dielectric film evaluating method of this invention comprises a stressing step of applying electrical stressing to a dielectric film in each of plural samples; a step of applying a voltage to the dielectric film in each of the plural samples so as to allow a current with a predetermined value to flow in the dielectric film; a step of monitoring a value of the voltage and measuring a threshold of the voltage obtained when breakdown occurs in the dielectric film; and a step of determining a breakdown threshold of the voltage by statistically processing plural thresholds of the voltage measured in the plural samples.

In still another aspect, the dielectric film evaluating method of this invention comprises a stressing step of applying electrical stressing to a dielectric film; a step of measuring a voltage applied to the dielectric film when an A mode stress induced leakage current has a predetermined value; and a lifetime predicting step of predicting a lifetime of the dielectric film on the basis of a relationship between the measured value of the voltage and a threshold of the voltage.

In still another aspect, the dielectric film evaluating method of this invention comprises a stressing step of applying electrical stressing to a dielectric film; a step of monitoring quality change of the dielectric film resulting from application of the electrical stressing by measuring an A mode stress induced leakage current; and a step of predicting a lifetime of the dielectric film on the basis of the monitored quality change of the dielectric film.

In still another aspect, the dielectric film evaluating method of this invention comprises a stressing step of applying a first voltage $V_0$ to a dielectric film; and a step of monitoring a value of a leakage current flowing in the dielectric film when a second voltage $V_m$ having an absolute value smaller than an absolute value of the first voltage $V_0$ is applied to the dielectric film, wherein the dielectric film is tested on the basis of a value of the leakage current.

Alternatively, the process estimating method of this invention comprises a step of measuring a level of an A mode stress induced leakage current flowing in a dielectric film in each of plural samples obtained under different process conditions; and a step of selecting a process condition for optimizing a lifetime of a dielectric film on the basis of the measured levels of the A mode stress induced leakage current in the plural samples.

Further alternatively, the dielectric film evaluating apparatus for practicing any of the dielectric film evaluating methods of this invention comprises a holder for holding a sample in which a dielectric film to be tested is formed; a probe to be brought in electrical contact with the sample placed on the holder; and a measurement unit for applying electrical stressing to the sample through the probe and measuring a current/voltage.

DETAILED DESCRIPTION OF THE INVENTION

It is known that a stress induced leakage current (hereinafter referred to as the "SILC") can be observed in two modes in ultra thin oxides, namely, in gate oxides with a thickness of approximately 6 nm or less (K. Okada, S. Kawasaki and Y. Hirofuji; Extended Abstracts of the 1994 International Conference on SOLID STATE DEVICES AND MATERIALS (1994) p.565). The currents in these two modes are distinguishably designated as an "A mode stress induced leakage current" and a "B mode stress induced leakage current", respectively. Herein, the A mode stress induced leakage current is referred to as the "A-SILC" and the B mode stress induced leakage current is referred to as the "B-SILC".

Figure 1:
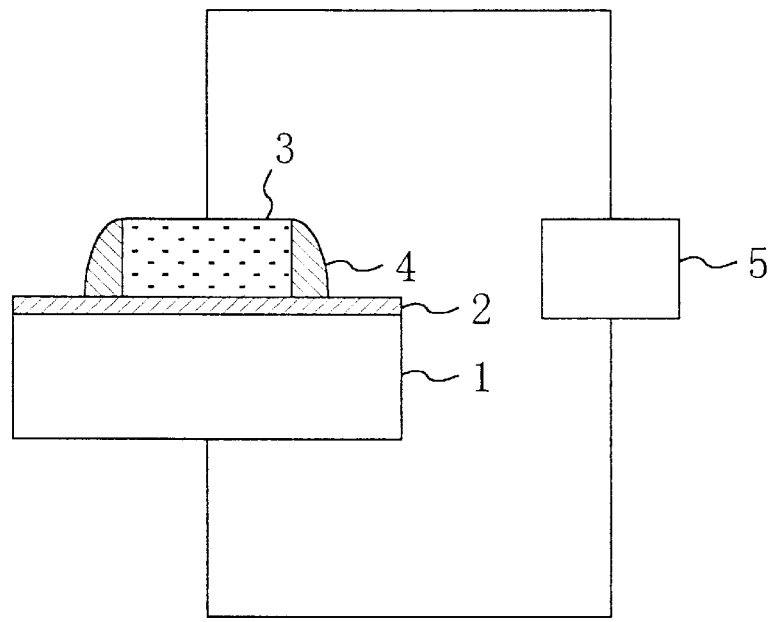
FIG. 1 is a sectional view for showing an exemplified structure of a sample used in a dielectric film evaluating method according to the invention.

FIG. 1 illustrates an exemplified sectional structure of a MOS capacitor used in a dielectric film evaluating method according to the invention. The MOS capacitor includes a gate oxide 2 having a thickness of 4.3 nm formed on a p-type single-crystalline silicon substrate 1, and a gate electrode 3 formed on the gate oxide 2. The gate electrode 3 having an area of 0.01 mm$^2$ is provided with dielectric sidewalls 4. The gate oxide 2 is formed by thermally oxidizing the surface of the silicon substrate 1, and the gate electrode 3 is formed by, for example, patterning a polysilicon film deposited by the CVD.

The silicon substrate 1 and the gate electrode 3 are electrically connected with a measurement unit of a dielectric film evaluating apparatus 5. Electrical stress can be given to the gate oxide 2 by repeatedly applying a negative voltage to the gate electrode 3.

Figure 2:
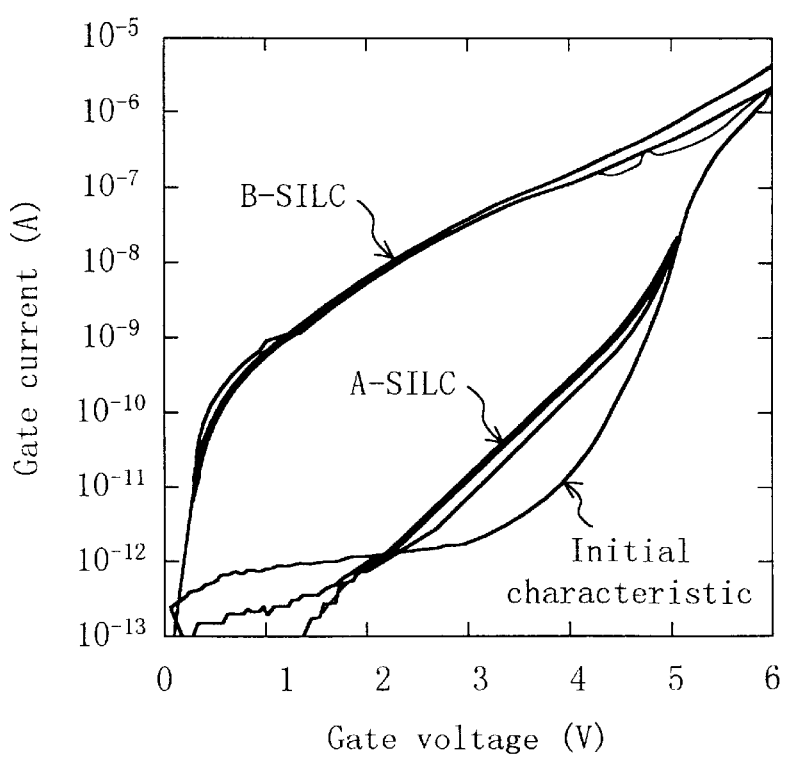
FIG. 2 is a graph for showing current-voltage characteristics of stress induced leakage currents in two modes in an ultra thin silicon dioxide.

FIG. 2 shows current-voltage characteristics of the gate oxide 2 in the MOS capacitor of FIG. 1. The current-voltage characteristic can be obtained by measuring leakage current (hereinafter sometimes referred to as the gate current) flowing from the silicon substrate 1 through the gate oxide 2 to the gate electrode 3 while variably applying a negative voltage to the gate electrode 3.

In FIG. 2, the typical A-SILC and B-SILC are observed. In an initial characteristic prior to the stressing, a Fowler-Nordheim (FN) tunnel current and a direct tunnel current are dominant. The A-SILC monotonously increases with the passage of the stressing time, followed by the abrupt appearance of the B-SILC. When the stressing is further continued, complete oxide breakdown occurs. This complete oxide breakdown is equivalent to dielectric breakdown observed in a comparatively thick dielectric film with a thickness of approximately 10 nm or more.

The A-SILC is a current flowing in the entire area of the oxide film. In contrast, the B-SILC is a current flowing through a local spot with a dimension of approximately several nm through several tens nm. The B-SILC is observed in a breakdown process in a ultra thin silicon dioxide(K. Okada and S. Kawasaki; Extended Abstracts of the 1995 International Conference on SOLID STATE DEVICES AND MATERIALS (1995) p. 473 and K. Okada; Extended Abstracts of the 1996 International Conference on SOLID STATE DEVICES AND MATERIALS (1996) p. 782). Accordingly, this phenomenon is designated as partial-breakdown (hereinafter referred to as the p-BD), and a reaction from the appearance of the B-SILC to the complete dielectric breakdown is designated as complete-breakdown (hereinafter referred to as the c-BD).

Also, there are some cases where the complete dielectric breakdown occurs without the appearance of the B-SILC. The p-BD is sometimes called as quasi-breakdown or soft-breakdown and the B-SILC is sometimes called as a quasi-breakdown current, but the words "A-SILC", "B-SILC", "p-BD" and "c-BD" are herein adopted.

The occurrence of the p-BD increases the leakage current but does not immediately stop the operation of the device. Therefore, a time up to the occurrence of the complete dielectric breakdown should be regarded as the lifetime of a gate oxide. However, the B-SILC can cause malfunction depending upon a device structure, and a time up to the p-BD should be regarded as the lifetime in a device strictly regulated in the leakage current level. Accordingly, it is significant for device evaluation to measure or predict the time up to the p-BD. Therefore, herein, the phenomenon of the occurrence of the p-BD and the phenomenon of the complete dielectric breakdown caused without the p-BD are both designated as the dielectric breakdown, and a time up to the thus defined dielectric breakdown is defined as the lifetime of a gate oxide.

Figure 3:
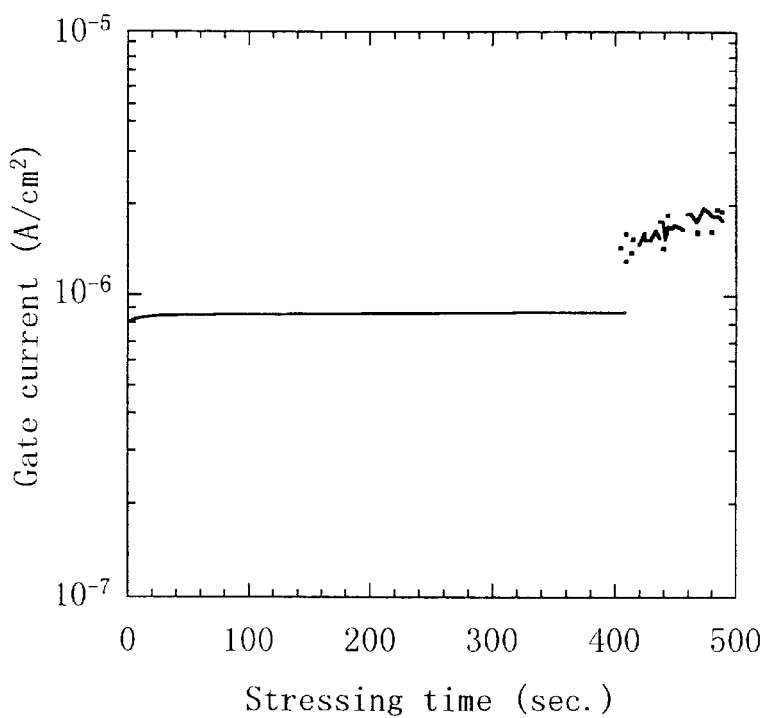
FIG. 3 is a graph for showing gate current flowing through a silicon dioxide film with a thickness of 4.3 nm, in which the constant gate voltage of −6 V is applied.

FIG. 3 shows a time dependence of a gate current under a constant voltage (−6 V) to the gate electrode 3 of the MOS capacitor of FIG. 1. In this sample, the p-BD occurs and the B-SILC is observed 410 seconds after the start of the application of the stressing voltage (−6 V). Under the stressing voltage, the gate current continuously increases with the passage of the stressing time, but the change is as small as approximately 8% increase from 0.823 $\mu$A to 0.889 $\mu$A for 410 seconds. It is known that this change is smaller as the oxide thickness is smaller. Accordingly, it is very difficult to predict the occurrence of the dielectric breakdown merely by monitoring the gate current. In the conventional evaluating method, such a gate current is monitored as described above, and hence, it is necessary to continuously apply the stressing voltage until the dielectric breakdown actually occurs. As a result, the measurement takes a long period of time.

In order to shorten the measurement time, the stressing condition is made more strict, namely, the absolute value of the stressing voltage is increased, or the temperature during the measurement is increased. This is designated as an electric field or temperature accelerated test. In this test, in order to predict the lifetime of a gate oxide under an actual usage condition for the device, it is necessary to find how the lifetime of the gate oxide is varied depending upon the electric field or the temperature. There are some models for the variation, but it has not been found out which model is correct. Furthermore, the lifetime of a gate oxide under the actual usage condition is obtained by extrapolating the lifetime obtained by the electric field or temperature accelerated test to the actual usage condition (the electric field or the temperature) of the device. Therefore, in order to accurately predict the lifetime, it is necessary to carry out the test in a lower electric field at a lower temperature.

As described above, a shorter measurement time can degrade the accuracy in the lifetime prediction, and therefore, the measurement time is inevitably very long in order to improve the accuracy.

Figure 4:
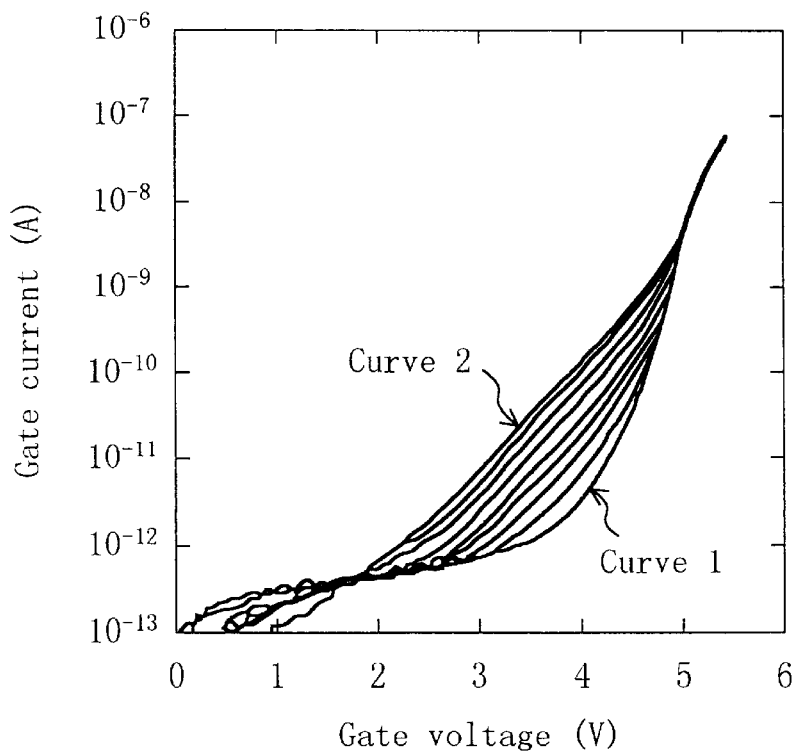
FIG. 4 is a graph for showing a current-voltage characteristic of a 4.3 nm-thick oxide under constant voltage stressing of −6 V.

FIG. 4 shows current-voltage characteristics obtained through the constant voltage stressing in a MOS capacitor including a silicon dioxide with a thickness of 4.3 nm. The stressing is performed by applying a constant voltage (−6 V) to the gate electrode of the MOS capacitor. Before the stressing, the MOS capacitor exhibits a characteristic shown with a curve 1. With the passage of the stressing time, a gate current in a region of a gate voltage between approximately −2 V and −5V, namely, the A-SILC, continuously increases, and a characteristic shown with a curve 2 is exhibited immediately before the p-BD. The gate current (A-SILC) is varied at the gate voltage of −4 V by two or more orders.

Figure 5:
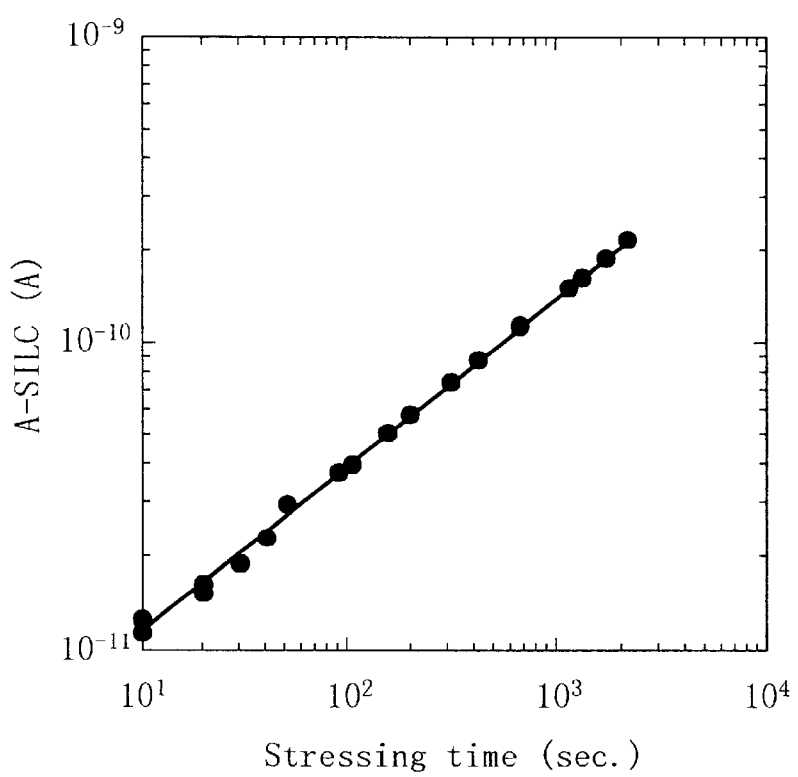
FIG. 5 is a graph for showing an A mode SILC at a gate voltage of −4 V as a function of stressing time.

FIG. 5 shows the gate current (A-SILC) at a gate voltage of −4 V as a function of time. In FIG. 5, the ordinate indicates the A-SILC obtained by applying the voltage of −4 V to the gate electrode of the above-described MOS capacitor, and the abscissa indicates the stressing time. As is obvious from FIG. 5, there is a linear relationship on a log-log scale between the gate current (A-SILC) and the stressing time.

Figure 6:
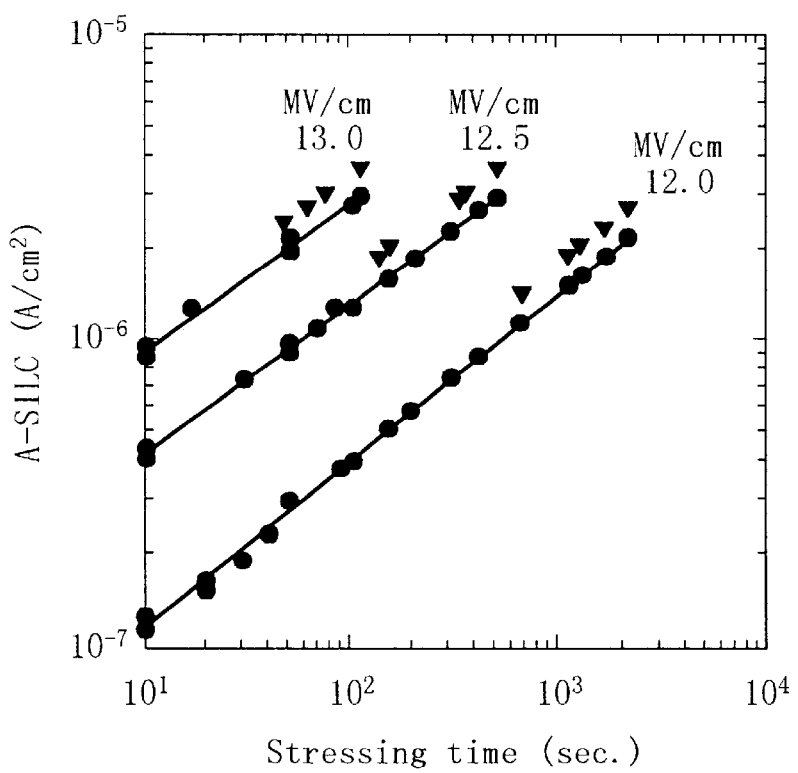
FIG. 6 is a graph for showing an A mode SILC at a gate voltage of −4 V as a function of stressing time for various electric fields.

FIG. 6 shows the A-SILC (at a gate voltage of −4 V) as a function of time under various stressing conditions. In the graph of FIG. 6, breakdown points are indicated with reverse black triangular marks (▼). The positions of lines are varied depending upon the applied electric field, but the slopes of the lines are constant. The time to the dielectric breakdown is varied depending upon the electric field strength, but the A-SILC flowing at the occurrence of the dielectric breakdown is substantially constant.

Figure 7:
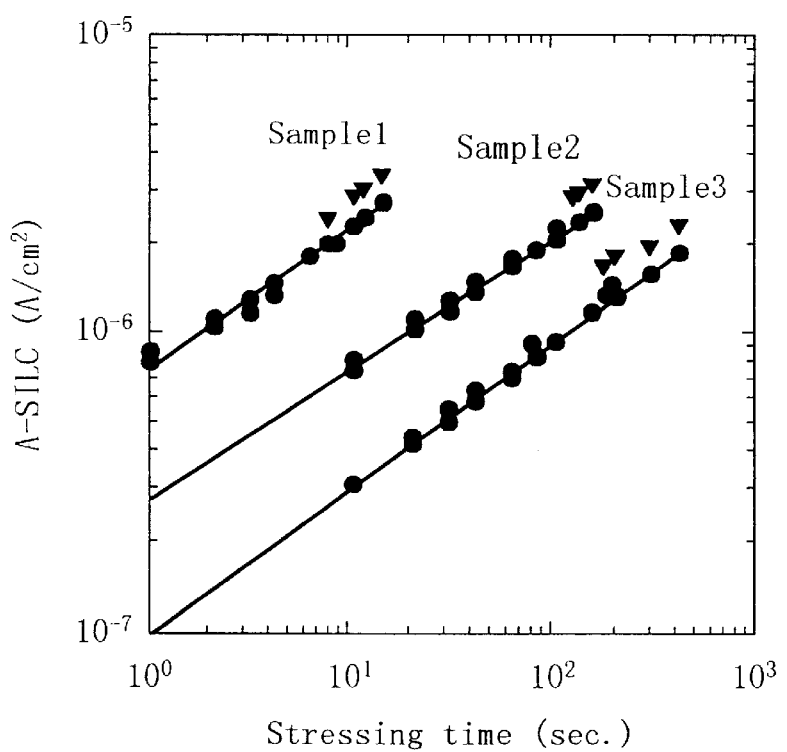
FIG. 7 is a graph for showing an A mode SILC at a gate voltage of −4 V as a function of stressing time for various electric fields for three samples having various oxide integity.

FIG. 7 shows the A-SILC (at a gate voltage of −4 V) as a function of time for three kinds of silicon dioxides (samples 1 through 3) having a thickness of 3.8 nm respectively. The samples are prepared through different fabrication processes. The stressing is performed by applying a constant voltage of −6 V to the gate electrode. The process conditions of fabricating the samples 1 through 3 are as follows. In the sample 1, the gate oxide is formed by dry oxidation at a loading temperature of 800° C., in the sample 2, the gate oxide is formed by pyrogenic at a loading temperature of 700° C., and in the sample 3, the gate oxide is formed by pyrogenic at a loading temperature of 500° C. The oxidation temperature is 800° C. in all the samples. Also in the graph of FIG. 7, the breakdown points are indicated with the reverse black triangular marks (▼). The positions of lines are varied depending upon the different fabrication processes, but the slopes of the lines are constant. Moreover, the time to the breakdown is different in the respective samples, but the A-SILC at the breakdown is substantially constant.

Since the lifetimes of the respective samples are slightly scattered, the A-SILCs obtained at the time of the dielectric breakdown are also scattered in the respective samples.

The present inventor has found a phenomenon that the A-SILC at the dielectric breakdown scarcely depends upon the stressing condition (such as the stressing voltage and the stressing current) and the fabrication process condition, and has found out a method of predicting the lifetime of a dielectric film by utilizing this phenomenon. Specifically, the A-SILC at the oxide breakdown are actually measured in plural samples and the measured values are used to determine a "threshold A-SILC for dielectric breakdown". This "threshold A-SILC" is optimally used for the lifetime prediction of oxide breakdown. This threshold is determined in consideration of scattering or spread of the measured values, so that a statistically reliable value for the lifetime prediction can be obtained. The use of "threshold A-SILC for dielectric breakdown" makes it possible to predict a lifetime of a thin oxide film without actually measuring the lifetimes of a large number of samples as in the conventional method.

On the basis of the study of the aforementioned breakdown mechanism of ultra thin films, the present invention provides dielectric film evaluating method and apparatus in which a time and the sample number required for measurement can be suppressed without degrading the reliability of the lifetime prediction.

Now, preferred embodiments of the dielectric film evaluating method of the invention will be described with reference to the accompanying drawings.

EMBODIMENT 1

Figure 8:
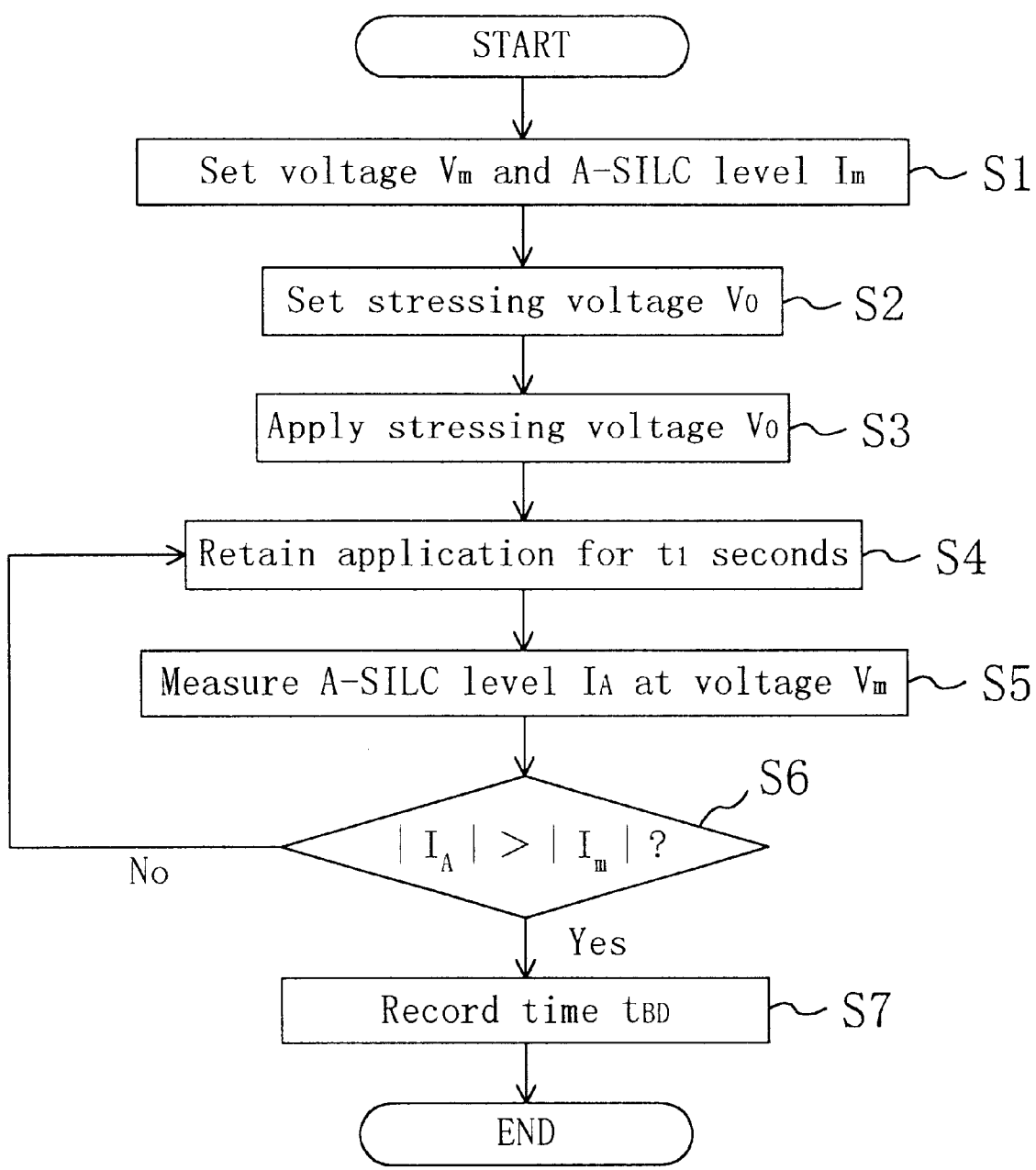
FIG. 8 is a flowchart for showing procedures in a dielectric film evaluating method according to a first embodiment of the invention.

A first embodiment will now be described with reference to a flowchart of FIG. 8.

In a method for evaluating dielectric films of this embodiment, a measurement voltage $V_m$ and a judgement A-SILC $I_m$ are first set in step S1. In step S2, a stressing voltage $V_0$ is set. The order of steps S1 and S2 can be reversed.

The measurement voltage $V_m$ is to be applied across a gate oxide when measuring an A-SILC. In this embodiment, the measurement voltage $V_m$ is set at −4 V. As the judgement value of A-SILC, one can use the A-SILC measured at the time when dielectric breakdown occurred in oxide films of the same kind and with the same thickness as those of the tested sample. The value of the judgement A-SILC $I_m$ corresponds to an expected value of A-SILC which will flow through the sample dielectric film at the time of the dielectric breakdown. The words "an A-SILC at the time of the dielectric breakdown" used herein means an A-SILC observed immediately before an abrupt increase of A-SILC. Alternatively, a value of an A-SILC which is determined by extrapolation of a straight line (or a curve) showing the A-SILC up to the time of the abrupt increase of A-SILC can be defined as "an A-SILC at the time of the dielectric breakdown".

Thus, the "A-SILC at the time of the dielectric breakdown" can be used as a "threshold A-SILC for dielectric breakdown". This "threshold" is predetermined in a manner described below before carrying out the dielectric film evaluating method of this embodiment. As the judgement value of A-SILC ($I_m$), a value comparatively approximate to the "threshold A-SILC for dielectric breakdown" can be used instead of the "threshold A-SILC for dielectric breakdown". For example, a value corresponding to 90% through 110% of the "threshold A-SILC for dielectric breakdown" can be used as the judgement value of A-SILC $I_m$. The stressing voltage $V_0$ is to be applied across the gate oxide film during the electrical stressing. In this embodiment, the stressing voltage $V_0$ is set at −6 V.

A gate current ($I_G$) might includes a direct tunnel current component and an FN current component. In the case where the gate current ($I_G$) includes such a current component ($I_{G0}$) other than an A-SILC component, a current level obtained by subtracting the current ($I_{G0}$) from the gate current ($I_G$) can be used as the A-SILC.

After steps S1 and S2, the stressing voltage $V_0$ is applied to the gate oxide in step S3 for electrical stressing. After the application of the stressing voltage $V_0$ to the gate oxide for a time duration of t1 seconds (step S4), an A-SILC $I_A$ is measured at the gate voltage $V_m$ in step S5. In step S6, it is determined whether or not the absolute value of the measured current $I_A$ exceeds the judgement value of the A-SILC $I_m$. The time duration for the application of the stressing voltage $V_0$ is not necessarily constant but can be increased on a log scale.

When it is determined in step S6 that the absolute value of the current $I_A$ does not exceed $I_m$, the measurement procedure returns to step S4 so that the steps S4 through S6 can be repeated.

When it is determined in step S6 that the absolute value of $I_A$ exceeds $I_m$, a total stressing time is recorded as a time $t_{BD}$. The time $t_{BD}$ corresponds to the lifetime of the tested oxide film because the oxide breakdown occurs at a high probability when the absolute value of $I_A$ exceeds $I_m$.

By performing such measurement merely once on one sample (a gate oxide in one MOS capacitor), it is possible to obtain the time $t_{BD}$ available for all of plural samples each including a dielectric film of the same kind and the same thickness as the tested oxide film. The "plural samples" herein includes another oxide film formed in another position in the silicon wafer which includes the tested oxide film. "Another oxide film" can be included in a different chip from that including the tested oxide film. Also, the "plural samples" can include a oxide film included in another silicon wafer obtained through substantially the same fabrication process as that for the silicon wafer including the tested oxide film.

In the aforementioned measurement, the stressing is continued until the dielectric breakdown, or p-BD, actually occurs in a given sample or until the A-SILC $I_A$ at which the dielectric breakdown can occur is observed.

Next, a method of determining the "judgement value of A-SILC $I_m$" or the "threshold of A-SILC for dielectric breakdown" will be described.

A behavior or time dependence of gate current is monitored in substantially the same manner as in the above measurement. The stressing is continued until the oxide breakdown actually occurs. When an abrupt increase in the gate current is detected, a gate current level measured immediately before the abrupt increase (namely, last in the monotonous and continuous increase of the gate current) is recorded as the "A-SILC at the time of the breakdown". Alternatively, a gate current level determined by extrapolating a straight line (or a curve) showing the gate current up to the time of the abrupt increase can be recorded as the "A-SILC at the time of the breakdown". This measurement procedure is performed on plural samples, for example, 20 through 100 samples.

In this manner, the data of the "A-SILC at the time of the breakdown" can be obtained with regard to the plural samples (plural dielectric films). These data are statistically processed to determine the "threshold A-SILC for dielectric breakdown".

Figure 9:
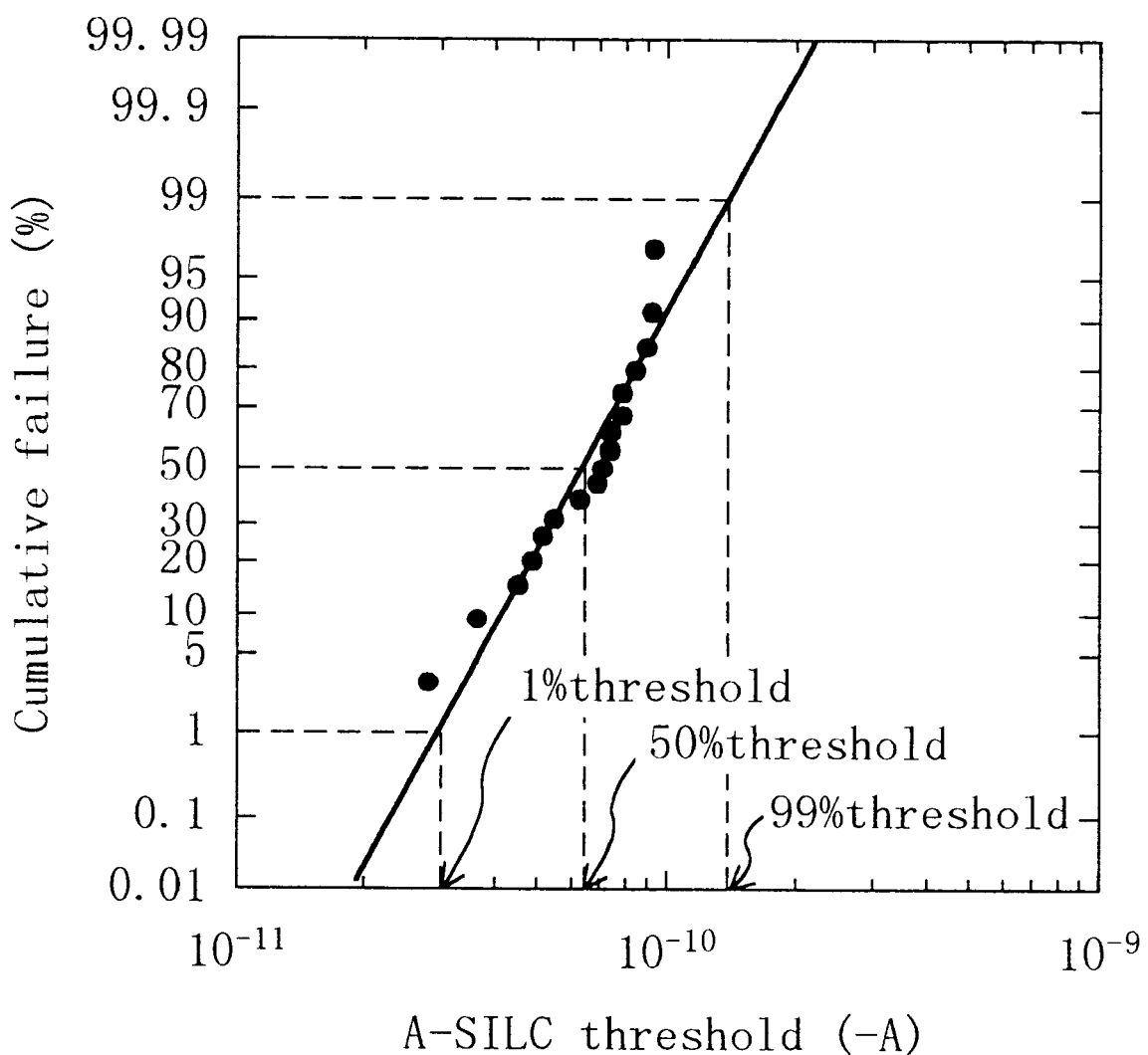
FIG. 9 is a graph of Weibull plotting.

FIG. 9 shows a relationship between the "A-SILC at the time of the dielectric breakdown" measured in plural samples and the cumulative percent failure, or cumulative percent of broken-down oxides. The graph of FIG. 9 is obtained through the Weibull plotting of values measured on seventeen MOS capacitors which are simultaneously formed in one silicon wafer. The measurement is performed by applying plural different stressing electric fields to the dielectric films.

In FIG. 9, a value referred to as a "50% threshold" corresponds to an A-SILC at which the dielectric breakdown occurs in 50% of all the samples (dielectric films). This "50% threshold" can be used as the judgement value of A-SILC $I_m$. A 50% breakdown lifetime $t_{BD}$ (or $t_{50}$) can be obtained by performing the measurement procedure steps as shown in FIG. 8 merely once.

In FIG. 9, values referred to as a "1% threshold" and a "99% threshold" correspond to an A-SILC at which the dielectric breakdown occurs in 1% of all the samples (dielectric films) and an A-SILC at which the dielectric breakdown occurs in 99% of all the samples (dielectric films), respectively.

When the relationship in FIG. 9 is obtained, an A-SILC corresponding to a desired cumulative percent breakdown can be used as the "threshold of A-SILC for dielectric breakdown".

It has been found that the "threshold A-SILC for dielectric breakdown" varies depending upon the area of a dielectric film and the temperature during the stressing. When the relationship between the threshold and the area of a dielectric film or the relationship between the threshold A-SILC and the temperature during the stressing is obtained, the threshold A-SILC can be corrected in accordance with the area of a dielectric film or the measurement.

As described the above, the A-SILC $I_A$ under stressing is monitored so that the lifetime of a dielectric film can be accurately measured in a shorter period of time. In this embodiment, the detection of the dielectric breakdown is made on the basis of whether or not the absolute value of the A-SILC $I_A$ exceeds the judgement value of A-SILC $I_m$. Instead of this, the breakdown detection can be made by monitoring a gate voltage necessary for allowing a given constant A-SILC to flow. This is because, when a given A-SILC flows across a gate oxide, a gate voltage applied to the gate oxide monotonously and continuously decreases with the passage of the stressing time and abruptly and discontinuously decreases when the dielectric breakdown (p-BD) occurs. The gate voltage also has a "threshold" correspondingly to the time of the dielectric breakdown. This threshold is also substantially constant regardless of the stressing condition and the manufacture process condition.

EMBODIMENT 2

Figure 10:
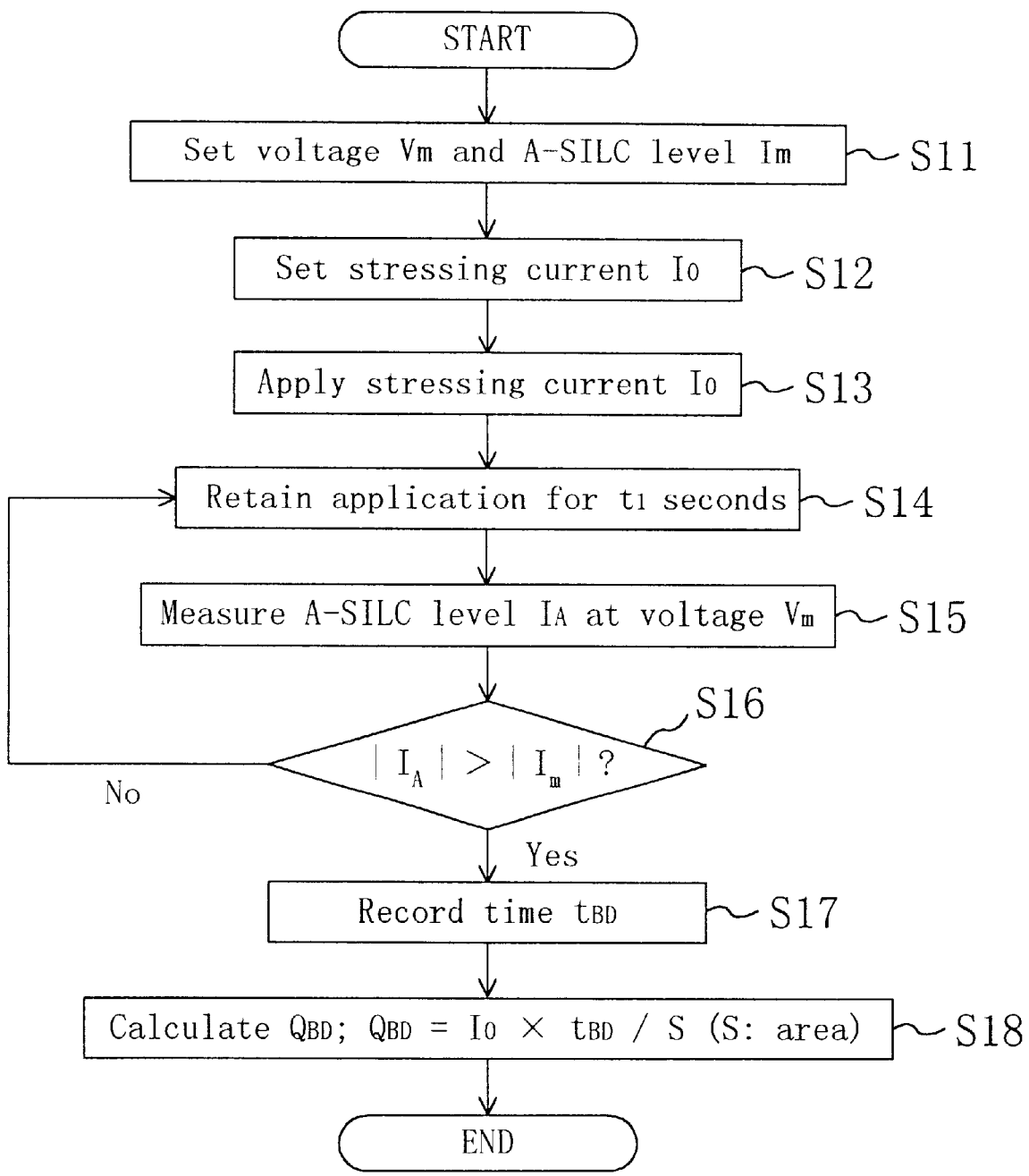
FIG. 10 is a flowchart for showing procedures in a dielectric film evaluating method according to a second embodiment of the invention.

A second embodiment will now be described with reference to a flowchart of FIG. 10.

In a method for evaluating dielectric films of this embodiment, a measurement voltage $V_m$ and a judgement value of A-SILC $I_m$ are first set in step S11, and a stressing current level $I_0$ is set in step S12. The "measurement voltage $V_m$" and the "judgment value of A-SILC $I_m$" are the same as those described in the first embodiment. The "stressing current level $I_0$" is to be applied to a dielectric film under a constant current stressing.

Next, in step S13, the stressing current ($I_0$) is applied to the dielectric film. After retaining the application of the stressing current ($I_0$) for a time duration of t1 seconds in step S14, an A-SILC $I_A$ at the voltage $V_m$ is measured in step S15. In step S16, it is determined whether or not the absolute value of $I_A$ exceeds $I_m$. When it is determined that the absolute value of $I_A$ does not exceed $I_m$, the measurement procedure returns to step S14, so that the steps S14 through S16 can be repeated.

When it is determined in step S16 that the absolute value of $I_A$ exceeds $I_m$, a total stressing time from the start of the application of the stressing current $I_0$ is recorded as a time $t_{BD}$ in step S17. A total injected charge $Q_{BD}$ is then calculated on the basis of the time $t_{BD}$ in step S18.

This embodiment is different from the first embodiment in applying the constant stressing current in stead of the constant stressing voltage to the dielectric film. In spite of this difference, the lifetime $t_{BD}$ of the dielectric film can be obtained basically in the same manner according to this embodiment. Accordingly, for the same reason as described in the first embodiment, the time $t_{BD}$ of all the samples including the tested sample can be obtained by performing the aforementioned measurement merely once. Also, in this embodiment, the total injected charge $Q_{BD}$ can be calculated with ease.

In this manner, according to this embodiment, the oxide lifetime can be accurately predicted in a shorter period of time by monitoring the A-SILC.

Although A-SILC at a constant gate voltage is monitored in this embodiment, a gate voltage required for a given A-SILC to flow can be monitored.

EMBODIMENT 3

A third embodiment will be described with reference to a flowchart of FIG. 11.

First, a measurement voltage $V_m$ and a judgement value of A-SILC $I_m$ are set in step S21, and a stressing condition and a stressing time $t_{total}$ are set in step S22. The "stressing condition" is, for example, the constant voltage stressing adopted in the first embodiment or the constant current stressing adopted in the second embodiment. The stressing can be performed at a high temperature which is elevated from room temperature so as to accelerate the measurement.

A stressing test is performed on a dielectric film in step S23 under the stressing condition set in step S22. When the stressing time $t_{total}$ elapses after the start of the application of the stressing to the dielectric film, the stressing test is completed. After completing the stressing test, A-SILCs $I_A$ recorded at respective stressing times t during the stressing test are plotted with regard to the stressing time t on a log-log scale in step S24. In step S25, a straight line is applied to the plotting on the log-log scale. In step S26, when the absolute value of the A-SILC $I_A$ exceeds the A-SILC $I_m$, a stressing time to the A-SILC $I_m$ is defined as a time $t_{BD}$. When the absolute value of the A-SILC $I_A$ does not exceed the A-SILC $I_m$, the straight line is extrapolated toward a longer time, so as to obtain a time to the A-SILC $I_m$.

Next, specific procedures of the stressing test performed in step S23 will be described with reference to FIG. 12.

First, in step S31, the stressing is applied to the dielectric film under the predetermined stressing condition. After retaining the application of the stressing for a time duration of t1 seconds (step S32), an A-SILC $I_A$ at the predetermined voltage $V_m$ (for example, −4 V) is measured in step S34, and the obtained current $I_A$ and time t are recorded in step S35. When the passage time from the start of the stressing test exceeds the predtermined stressing time $t_{total}$ (step S36), the stressing is completed and the stressing test is completed. When the passage time from the start of the stressing test does not exceed the predtermined stressing time $t_{total}$ in step S36, the process returns to step S32, so that the procedures in steps S32, S34, S35 and S36 can be repeated. The time t1 is, for example, 0.1 through 10 seconds, and the stressing time $t_{total}$ is, for example, 10 through 10000 seconds.

In this embodiment, there is no need to apply the stressing to the sample until the breakdown of the dielectric film is actually caused. As the stressing time $t_{total}$, a time sufficiently shorter than the aforementioned lifetime $t_{BD}$ of the dielectric film can be set. In this embodiment, considering that there is a linear relationship on the log-log scale as is shown in FIGS. 6 and 7 between the A-SILC $I_A$ and the stressing time t, the lifetime of the dielectric film is predicted. This prediction is on the basis of the fact that the dielectric breakdown occurs when the A-SILC $I_A$ exceeds the dielectric breakdown threshold.

For the same reason as described in the first embodiment, the time $t_{BD}$ of all samples can be obtained by performing the aforementioned measurement merely once.

In this embodiment, in stead of plotting the A-SILC IA, a gate voltage value required for a given A-SILC to flow can be used.

In this manner, according to this embodiment, the lifetime of a gate oxide can be accurately predicted in a shorter period of time. Since there is no need to continue the stressing test until the breakdown is actually caused in the dielectric film in this embodiment, the time required for the test can be shortened. Thus this embodiment is superior to the first embodiment.

Figure 13:
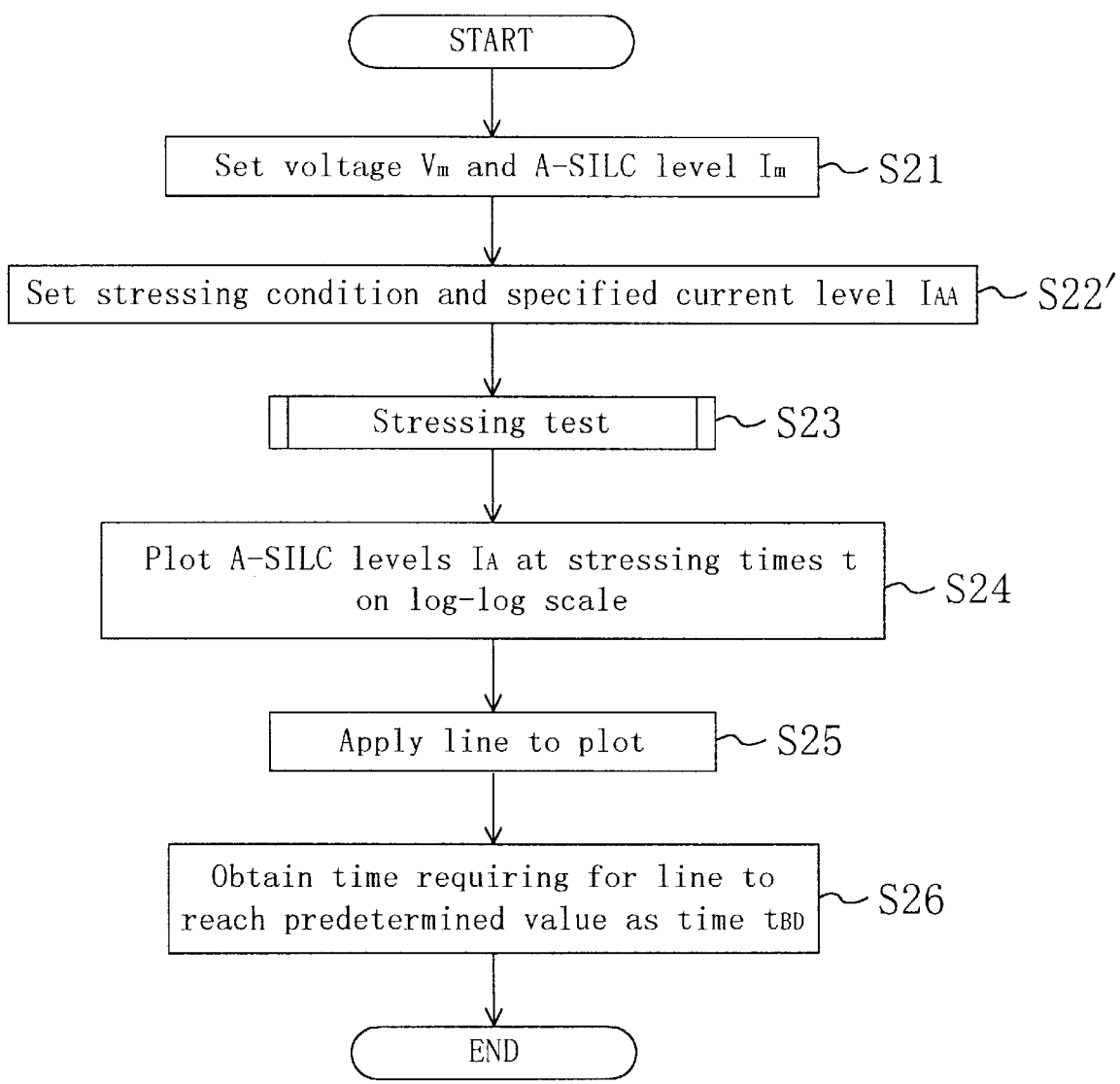
FIG. 13 is a flowchart for showing modified procedures in the dielectric film evaluating method according to the third embodiment.
Figure 14:
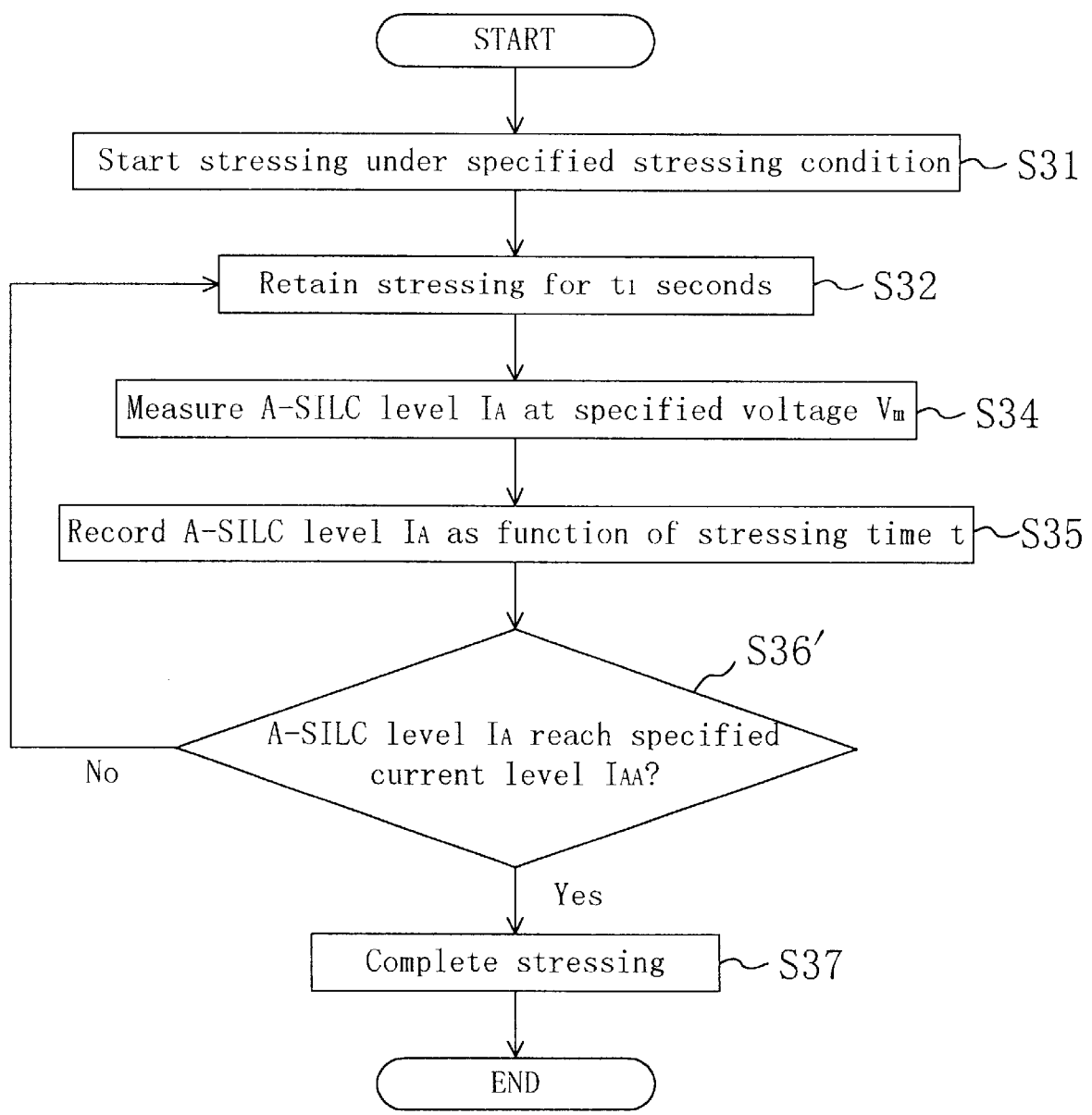
FIG. 14 is a flowchart for showing modified procedures of the stressing test conducted in the dielectric film evaluating method of the invention.
Figure 15:
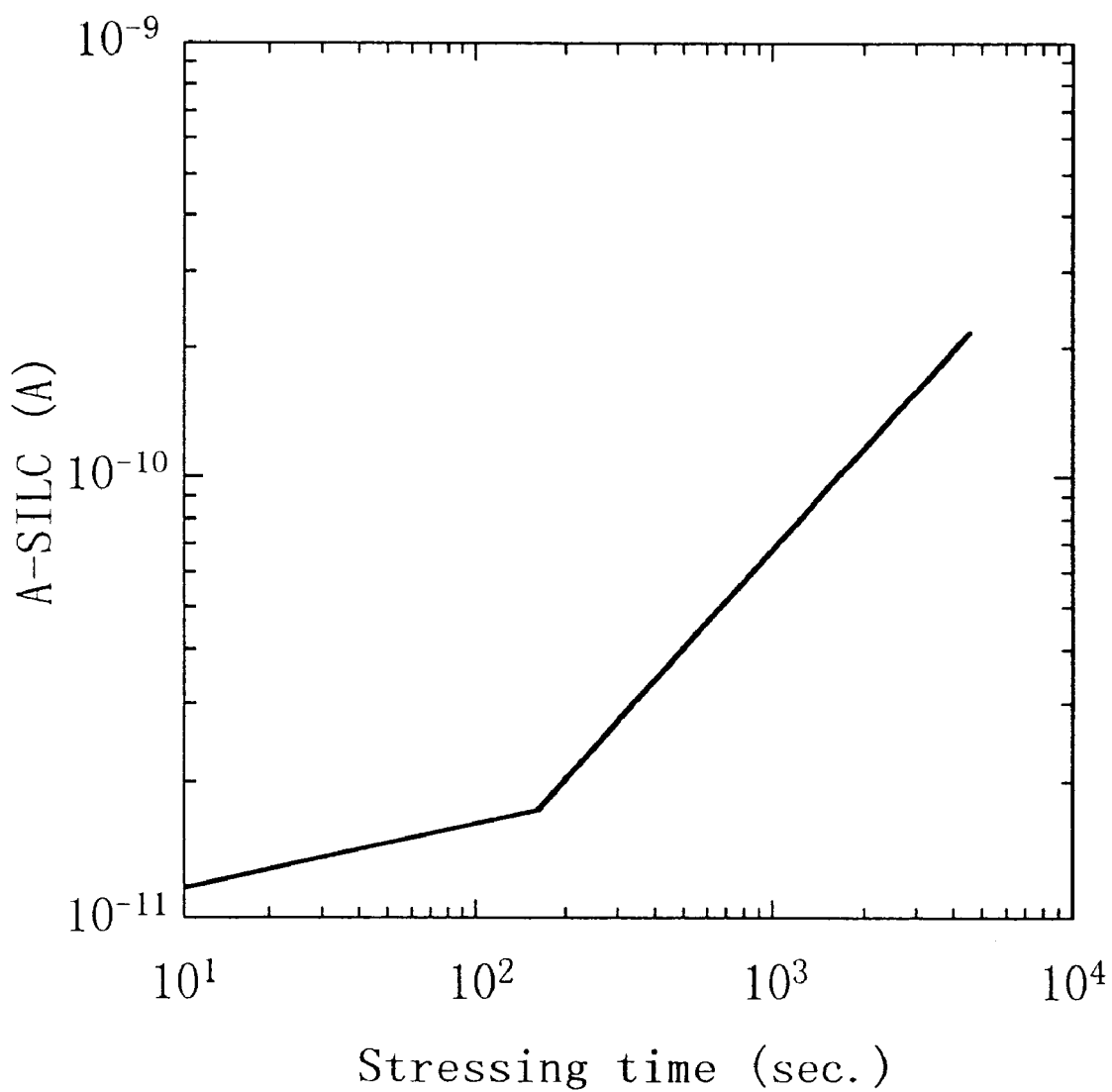
FIG. 15 is a graph for showing an A mode SILC at a gate voltage of −4 V obtained by applying comparatively small electrical stressing to a silicon dioxide.

In this embodiment, the stressing test is completed when the passage time from the start of the stressing test exceeds the predetermined stressing time $t_{total}$. Instead, the stressing test can be completed when the A-SILC $I_A$ exceeds a previously set current level $I_{AA}$. FIGS. 13 and 14 show procedures adopted in this case, wherein steps S22 and S36 of FIGS. 11 and 12 are replaced with steps S22' and S36', respectively. The process shown in FIGS. 13 and 14 is particularly effective when there is a relationship as is shown in FIG. 15 between the A-SILC $I_A$ and the stressing time. This is because, when the set time $t_{total}$ is too short, there is a possibility that the stressing test is completed before observing substantial increase of the A-SILC $I_A$ due to degradation of the dielectric film. When the electrical stressing applied to the dielectric film is comparatively small, the A-SILC $I_A$ can vary as is shown in FIG. 15.

EMBODIMENT 4

Figure 16:
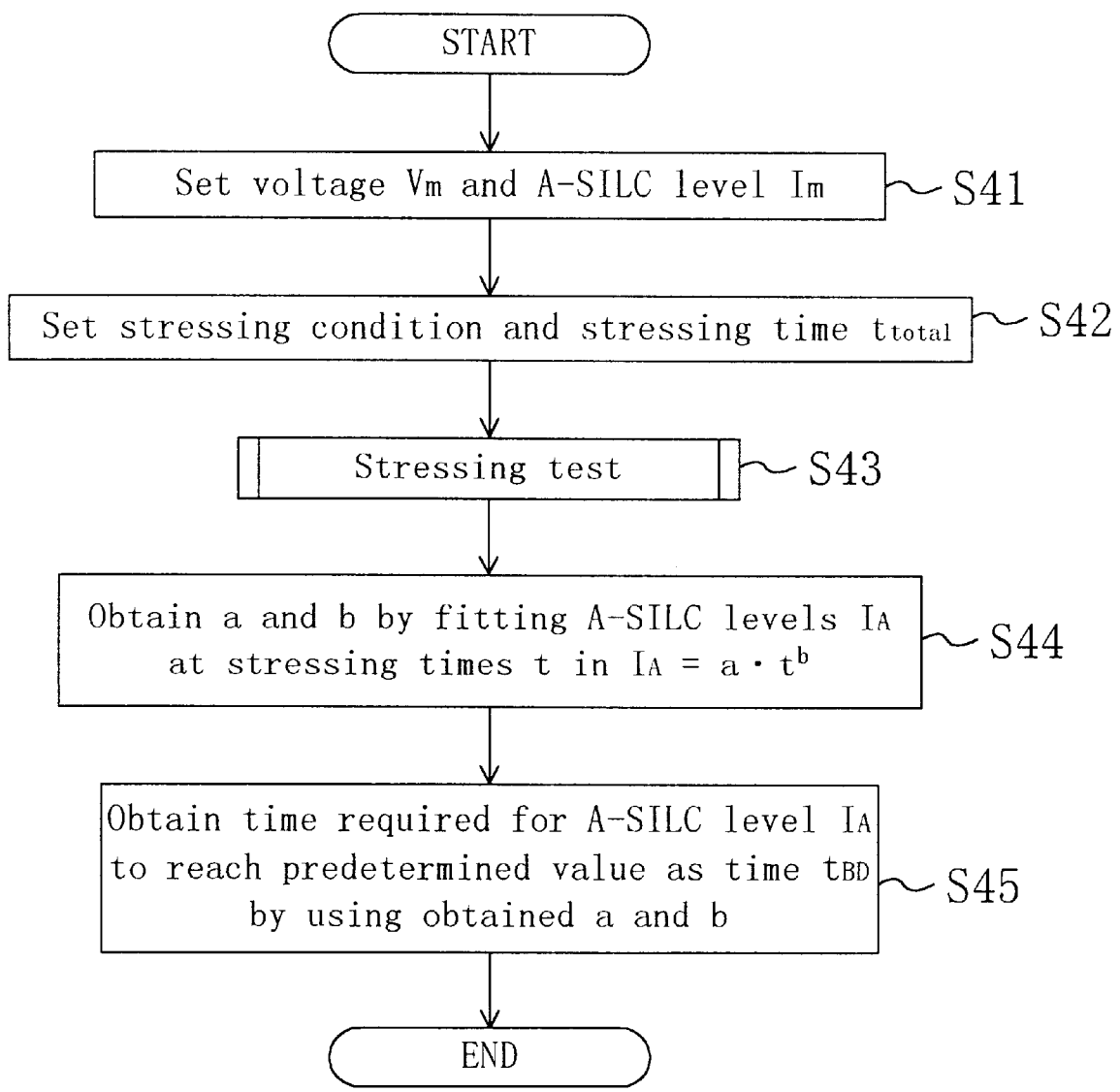
FIG. 16 is a flowchart for showing procedures in a dielectric film evaluating method according to a fourth embodiment of the invention.

A fourth embodiment will now be described with reference to a flowchart of FIG. 16.

First, a measurement voltage $V_m$ and a judgement value of A-SILC $I_m$ are set in step S41, and a stressing condition and a stressing time $t_{total}$ are set in step S42. A stressing test is performed on a dielectric film under the stress condition set in step S42 (step S43). After completing the stressing test, in step S44, an A-SILC $I_A$ recorded at each stressing time t during the stressing test is substituted in the following expression (2) or (3), thereby executing fitting:

$$I_A = a \times t^b \tag{2}$$

$$\log(I_A) = \log(a) + b \cdot \log(t) \tag{3}$$

wherein $I_A$ indicates the A-SILC, t indicates the stressing time, and a and b indicate fitting parameters.

Through the fitting, the values of the parameters a and b can be determined. Next, the values of the parameters a and b obtained in step S44 are substituted in the expression (2), so as to calculate a stressing time t required for the current level $I_A$ to reach a previously set value (i.e., the A-SILC $I_m$). Thus, a time $t_{BD}$ to breakdown can be obtained (step S45).

Figure 11:
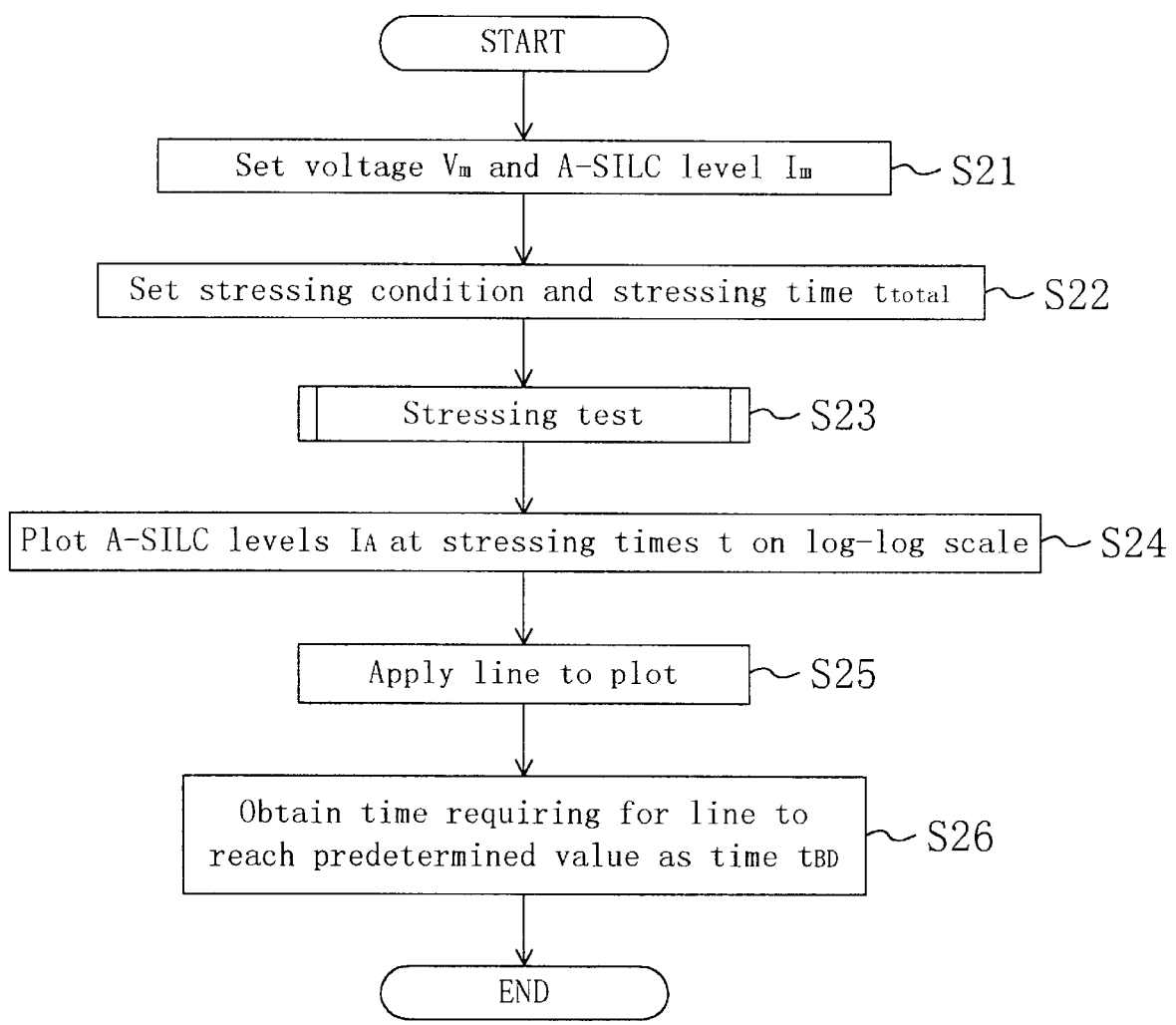
FIG. 11 is a flowchart for showing procedures in a dielectric film evaluating method according to a third embodiment of the invention.
Figure 12:
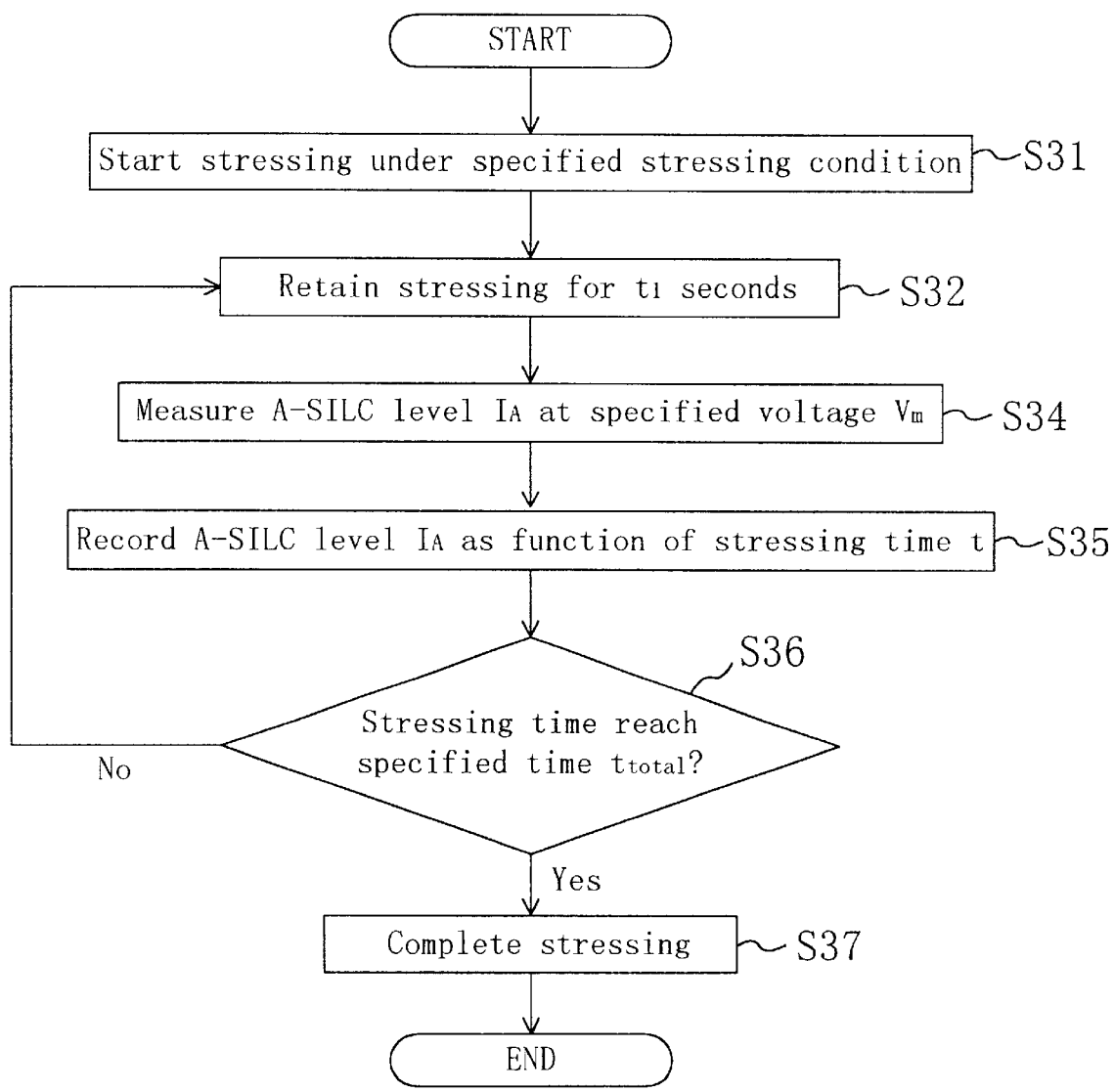
FIG. 12 is a flowchart for showing exemplified procedures of a stressing test conducted in the dielectric film evaluating method of the invention.

The specific procedures of the stressing test performed in step S43 can be the same as those of the stressing test of FIG. 11 (shown in the flowchart of FIG. 12 or 14).

Also in this embodiment, for the same reason as described in the first embodiment, the time $t_{BD}$ of all samples can be obtained by conducting the aforementioned measurement merely once. In stead of using the A-SILC IA, a gate voltage value required for a given A-SILC to flow can be used.

Also, as described in the third embodiment, in stead of completing the stressing test when the passage time from the start of the stressing test exceeds the predetermined time $t_{total}$, the stressing test can be completed when the A-SILC $I_A$ exceeds a previously predetermined current level $I_{AA}$.

According to this embodiment, the oxide lifetime can be accurately predicted in a shorter period of time. This embodiment is superior to the first embodiment because the time required for the test can be shortened since there is no need to continue the stressing test until the breakdown is actually caused in the dielectric film in this embodiment. Furthermore, the value of the fitting parameters a and b can be obtained by using the expressions, and it is possible to judge the appropriateness of the measured or predicted lifetime by checking the values of the parameters a and b. In view of this, this embodiment is superior to the third embodiment.

In the case where the relationship between the stressing time t and the A-SILC $I_A$ can be more preferably fit by using another expression different from the aforementioned expressions, the expression (2) or (3) is appropriately replaced with another expression or compensated. In the graph of FIG. 6 or 7, there is a linear relationship between the stressing time t and the A-SILC $I_A$, but in some cases, the line has different slopes between a region where the A-SILC $I_A$ is comparatively small and a region where it is comparatively large. Accordingly, the relationship between the stressing time t and the A-SILC $I_A$ is not limited to those shown in FIGS. 6 and 7.

EMBODIMENT 5
(Dielectric Film Evaluating Apparatus)

Now, a dielectric film evaluating apparatus used for carrying out the dielectric film evaluation method of the present invention will be described with reference to FIG. 17.

Figure 17:
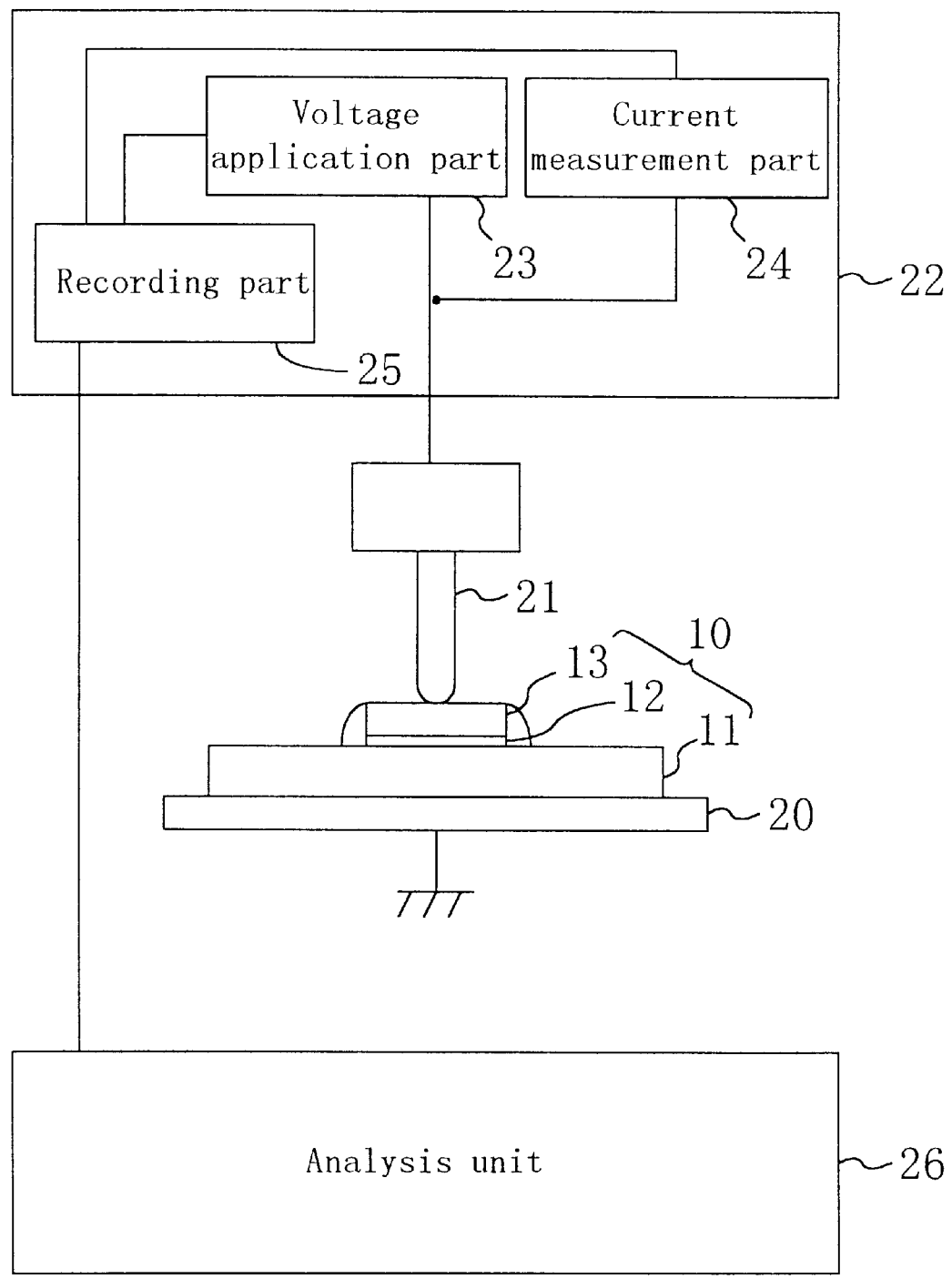
FIG. 17 is a schematic block diagram for showing an exemplified structure of a dielectric film evaluating apparatus according to the invention.
Figure 18:
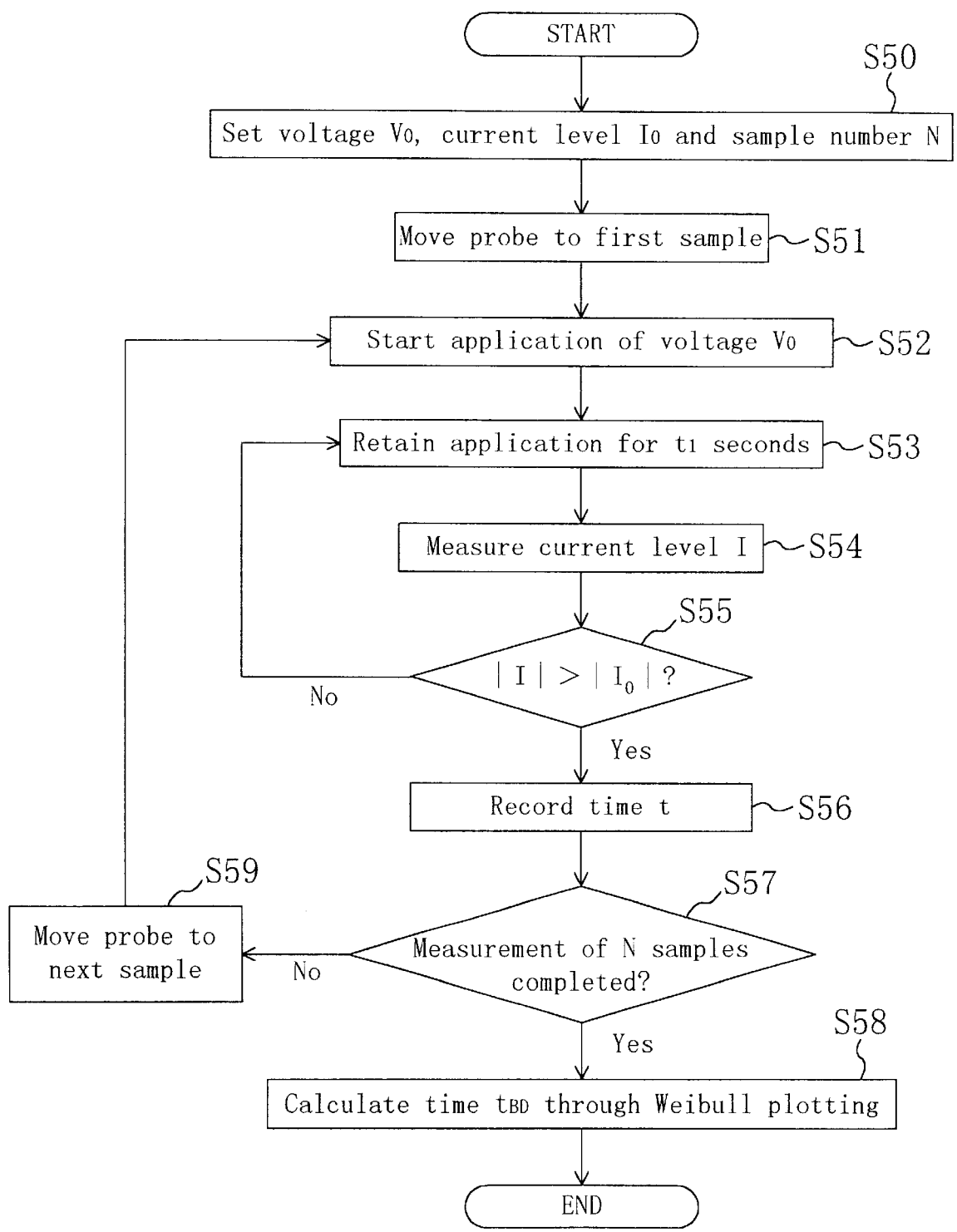
FIG. 18 is a flowchart for showing procedures in a conventional evaluating method for the reliability of a dielectric film.
Figure 19:
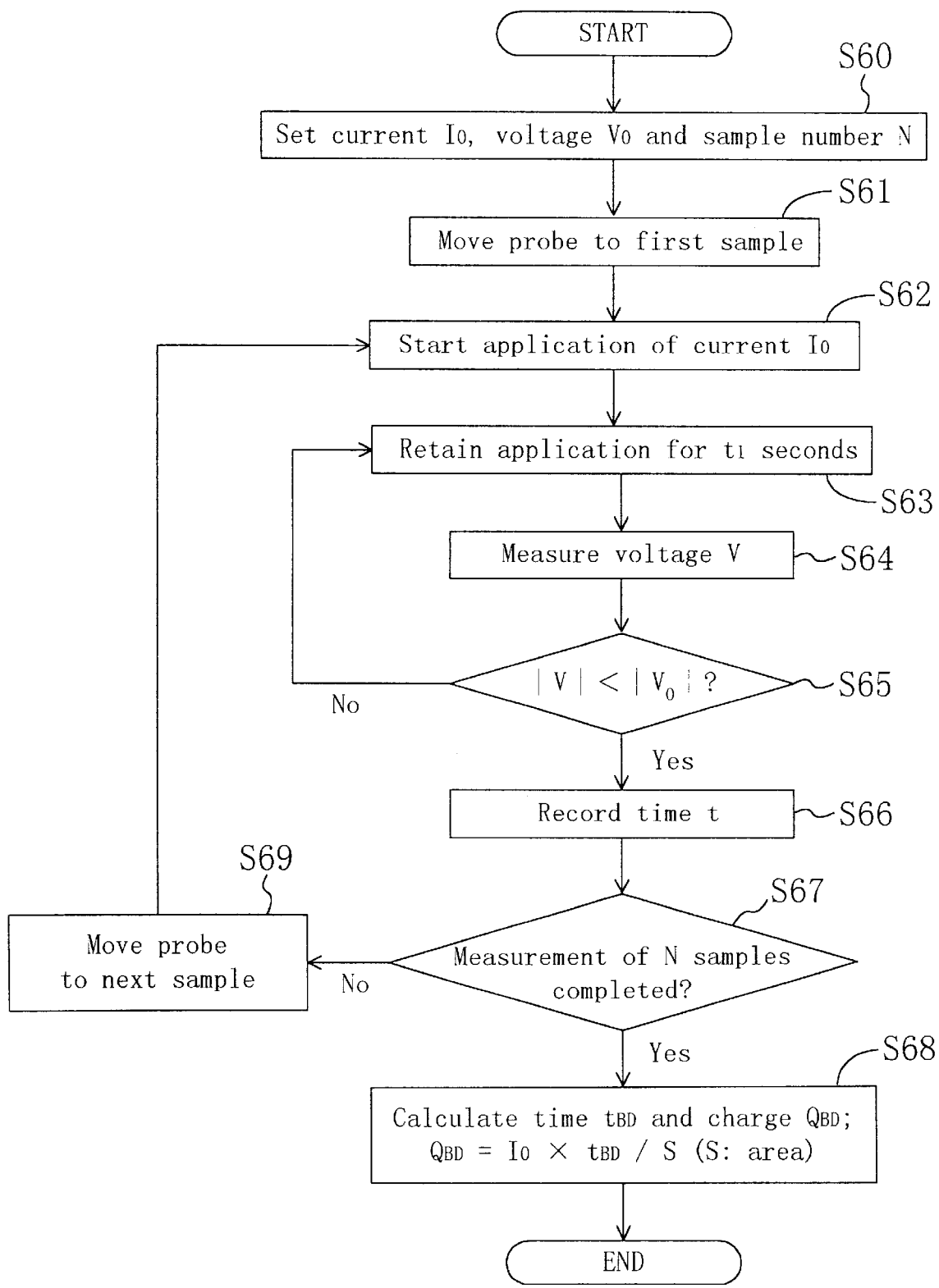
FIG. 19 is a flowchart for showing procedures in another conventional evaluating method for the reliability of a dielectric film.

The dielectric film evaluating apparatus of FIG. 17 includes a sample holder 20 for holding a sample 10, a probe 21 to be brought in an electrical contact with the sample 10 placed on the sample holder 20, a measurement unit 22 for applying electrical stressing to the sample 10 through the probe 21 and measuring a current/voltage, and an analysis unit 26 for analyzing obtained data.

The sample 10 includes a silicon substrate 11, a gate oxide 12 formed on the substrate 11 and a gate electrode 13 formed on the gate oxide 12. The holder 20 for holding the sample 10 is provided with a heater for heating the sample 10 during the stressing process. The holder 20 is electrically connected with the silicon substrate 11 of the sample 10 and is also grounded.

The measurement unit 22 includes a voltage application part 23, a current measurement part 24 and a recording part 25. The voltage application part 23 applies a stressing voltage $V_0$ (of, for example, −6 V) to the sample 10 in the stressing process and applies a measurement voltage $V_m$ (of, for example, −4 V) to the sample 10 in a process for measuring an A-SILC $I_A$. The current measurement part 24 measures a current flowing in the dielectric film 12 under application of the measurement voltage $V_m$ to the sample 10 in the process for measuring the A-SILC $I_A$. The measured A-SILC $I_A$ is recorded in reference to a measurement time (stressing time t) in the recording part 25. In the case of the constant current stressing, a constant current is supplied to the sample from a constant current supply unit not shown.

In carrying out the method of the fourth embodiment, the aforementioned fitting is performed on the data recorded in the recording part 25 by a microprocessor in the analysis unit 26. When the fitting parameters a and b are obtained and a previously set value (the A-SILC $I_m$) is given, the time $t_{BD}$ can be calculated.

In each of the aforementioned embodiments, the lifetime of a dielectric film is predicted on the assumption that the A-SILC $I_m$ or the threshold A-SILC for dielectric breakdown is constant regardless of the stressing condition and the process condition. However, it is known that the threshold A-SILC for dielectric breakdown varies in accordance with the temperature during the measurement. Therefore, the threshold A-SILC for dielectric breakdown can be expressed as a function of the temperature.

Furthermore, the present invention is applicable to a method of selecting an optimal fabrication process condition in view of the lifetime and reliability of a dielectric film. As is shown in FIG. 7, the relationship between the stressing time and the A-SILC is largely varied even in the same dielectric film depending upon different fabrication process conditions adopted for forming the dielectric film. The graph of FIG. 7 reveals that the fabrication process condition adopted for the sample 3 is most preferable as compared with the fabrication process conditions for the other samples. The process condition for the sample 3 can elongate the oxide lifetime. By measuring an A-SILC at a fixed time of, for example, $t_x$ seconds in each of samples obtained under different fabrication process conditions and comparing the measured values, it is possible to select a fabrication process condition optimal for improving the reliability of the dielectric film.

As described so far, a dielectric film evaluating method of this invention includes a stressing step of applying stressing to a dielectric film; and a step of monitoring an A mode stress induced leakage current and measuring a value of the A mode stress induced leakage current flowing when the breakdown occurs in the dielectric film. As a result, the A mode stress induced leakage current at the time of the dielectric breakdown can be obtained.

Alternatively, another dielectric film evaluating method of this invention includes a step of measuring a value of an A mode stress induced leakage current flowing when the breakdown occurs in a dielectric film in each of plural samples; and a threshold determining step of determining a dielectric breakdown threshold of the A mode stress induced leakage current by statistically processing the measured plural values. As a result, a useful threshold or judgement value usable for predicting the lifetime of the dielectric film can be obtained.

Furthermore, still another dielectric film evaluating method of this invention includes a step of measuring an A mode stress induced leakage current; and a lifetime predicting step of predicting the lifetime of a dielectric film on the basis of a relationship between the measured value of the A mode stress induced leakage current and a dielectric breakdown threshold of the A mode stress induced leakage current. As a result, the lifetime of the dielectric film can be predicted without continuing the stressing until the dielectric breakdown is actually caused.

In this manner, according to the present invention, the time and the sample number required for the measurement can be suppressed without degrading the reliability of the measurement result. As a result, the lifetime of an oxide can be highly accurately predicted in a shorter period of time.

What is claimed is:

1. A dielectric film evaluating method comprising the steps of:

repeatedly applying electrical stress of a first voltage or a first current to each of a plurality of sample dielectric films formed similarly to a target dielectric film, which is to be evaluated, for a first period of time, and repeatedly measuring an A mode stress induced leakage current (A-SILC) flowing through each of the sample dielectric films, thereby obtaining a respective specific A-SILC value for each of the plurality of sample dielectric films, each of the specific A-SILC values being a value which the A-SILC has when breakdown occurs in each of the plurality of sample dielectric films;

and determining a breakdown threshold A-SILC of the target dielectric film by conducting a statistical analysis on the specific A-SILC value of the sample dielectric films.

2. The dielectric film evaluating method of claim 1, wherein the step of determining the breakdown threshold A-SILC of the target dielectric film includes a step of defining a relationship between the specific A-SILC values of the sample dielectric films and a cumulative failure, to assign, as the breakdown threshold A-SILC of the target dielectric film, an A-SILC value which is obtained when the cumulative failure is equal to a predetermined value in accordance with the defined relationship.

3. The dielectric film evaluating method of claim 1, wherein the breakdown threshold A-SILC of the target dielectric film is indicated using a function of temperature at which the electrical stress is applied to the plurality of sample dielectric films.

4. The dielectric film evaluating method of claim 1, further comprising, after the step of determining the breakdown threshold A-SILC of the target dielectric film;

a step of repeatedly applying electric stress of the first voltage, a second voltage, the first current or a second current to the target dielectric film for the first period of time or a second period of time and repeatedly measuring an A-SILC flowing through the target dielectric film, until an A-SILC value which is equal to, or larger than, the breakdown threshold A-SILC of the target dielectric film or a judgement value determined based thereon, is measured; and a step of calculating a total time for the electrical stress application which is repeatedly performed on the target dielectric film, as a lifetime of the target dielectric film.

5. The dielectric film evaluating method of claim 4, wherein the electrical stress applied to the target dielectric film is the first or second current;

the method further comprising, after the step of calculating the total time for the electrical stress application to the target dielectric film, a step of calculating a total amount of electric charges which are supplied to the target dielectric film until breakdown occurs in the target dielectric film, based on the first or second current and the lifetime of the target dielectric film.

6. The dielectric film evaluating method of claim 1, further comprising, after the step of determining the breakdown threshold A-SILC of the target dielectric film:

a step of repeatedly applying electrical stress of the first voltage, a second voltage, the first current or a second current to the target dielectric film for the first period of time or a second period of time and repeatedly measuring an A-SILC flowing through the target dielectric film, a step of defining a relationship between the measured A-SILC flowing through the target dielectric film and a total time for the electrical stress application which is repeatedly performed on the target dielectric film; and a step of calculating, as a lifetime of the target dielectric film, an amount of time from the beginning of the electrical stress application to the target dielectric film to a time when an A-SILC of the target dielectric film has a value which is equal to, or larger than, the breakdown threshold A-SILC of the target dielectric film or a judgment value determined based thereon in accordance with the defined relationship.

7. The dielectric film evaluating method of claim 6, wherein the measurement of A-SILC flowing though the target dielectric film is repeatedly performed until the total time for the electrical stress application to the target dielectric film is equal to, or larger than, a predetermined time.

8. The dielectric film evaluating method of claim 6, wherein the measurement of A-SILC flowing through the target dielectric film is repeatedly performed until an A-SILC value of the target dielectric film which is equal to, or larger than, a predetermined value is measured.

9. The dielectric film evaluating method of claim 6, wherein:

the relationship between the measured A-SILC flowing through the target dielectric film and the total time for the electrical stress application to the target dielectric film is defined by plotting the measured A-SILC values and the total time on a log-log scale and applying a straight line to a result from the plotting.

10. The dielectric film evaluating method of claim 6 wherein:

the relationship between the measured A-SILC values flowing through the target dielectric film and the total time for the electrical stress application to the target dielectric film is represented as $I_A = a \times t^b$, where $I_A$ is any of the measured A-SILC values flowing through the target dielectric film, t is the total time for the electrical stress application to the target dielectric film, and each of a and b is a constant.

11. A dielectric film evaluating apparatus for practicing the dielectric film evaluating method of claim 1, comprising:

a holder for holding a sample in which a dielectric film to be evaluated is formed;

a probe to be brought in electrical contact with the sample placed on the holder; and a measurement unit for applying an electrical stress to the sample through the probe and measuring a current or voltage.

12. A dielectric film evaluating apparatus for practicing the dielectric film evaluating method of claim 6, comprising:

a holder for holding a sample in which a dielectric film to be evaluated is formed;

a probe to be brought in electrical contact with the sample placed on the holder; and a measurement unit for applying an electrical stress to the sample through the probe and measuring a current or voltage.

13. The dielectric film evaluating apparatus of claim 11, further comprising an analysis unit for analyzing data obtained by the measurement unit.

14. The dielectric film evaluating apparatus of claim 12, further comprising an analysis unit for analyzing data obtained by the measurement unit.

* * * * *